US012698287B2

(12) United States Patent
Zeng et al.

(10) Patent No.: US 12,698,287 B2
(45) Date of Patent: Aug. 4, 2026

(54) ARYL-FUSED ISOSELENAZOLE COMPOUND CONTAINING TETRAZINE SUBSTITUENT, SYNTHESIS METHOD THEREFOR, AND USE THEREOF

(71) Applicant: KEAISE MEDICINE WUHAN CORP., Wuhan (CN)

(72) Inventors: Huihui Zeng, Wuhan (CN); Wenxuan Jiao, Wuhan (CN); Hanwei Yin, Wuhan (CN)

(73) Assignee: KEAISE MEDICINE WUHAN CORP., Wuhan (CN)

( * ) Notice: Subject to any disclaimer, the term of this patent is extended or adjusted under 35 U.S.C. 154(b) by 872 days.

(21) Appl. No.: 17/995,411

(22) PCT Filed: Apr. 12, 2021

(86) PCT No.: PCT/CN2021/086688

§ 371 (c)(1),
(2) Date: Oct. 4, 2022

(87) PCT Pub. No.: WO2021/208865

PCT Pub. Date: Oct. 21, 2021

(65) Prior Publication Data

US 2023/0167120 A1 Jun. 1, 2023

(30) Foreign Application Priority Data

Apr. 13, 2020 (CN) ......................... 202010287745.6

(51) Int. Cl.

*C07D 487/04* (2006.01)
*A61P 25/00* (2006.01)
*A61P 35/00* (2006.01)

(52) U.S. Cl.

CPC ............ *C07D 487/04* (2013.01); *A61P 25/00* (2018.01); *A61P 35/00* (2018.01)

(58) Field of Classification Search

CPC ......... C07D 487/04; A61P 25/00; A61P 35/00
See application file for complete search history.

(56) References Cited

FOREIGN PATENT DOCUMENTS

| | | | |
|---|---|---|---|
| CN | 102234254 | A | 11/2011 |
| CN | 106699687 | A | 5/2017 |
| CN | 106977472 | A | 7/2017 |
| CN | 108503607 | A | 9/2018 |
| WO | 2017084598 | A1 | 5/2017 |
| WO | 2021223780 | A2 | 11/2021 |

OTHER PUBLICATIONS

Mao, Fei, et al. "Novel tacrine-ebselen hybrids with improved cholinesterase inhibitory, hydrogen peroxide and peroxynitrite scavenging activity." Bioorganic & medicinal chemistry letters 23.24 (2013): 6737-6742. (Year: 2013).*

Yan, Jun et al., "Design, Synthesis, and Biological Evaluation of Benzoselenazole-stilbene Hybrids as Multi-target-directed Anticancer Agents", European Journal of Medicinal Chemistry, Mar. 14, 2015; ISSN:0223-5234; pp. 221-223.

Mao, Fei et al., "Novel tacrine-ebselen hybrids with improved cholinesterase inhibitory, hydrogen peroxide and peroxynitrite scavenging activity"; Bioorganic & Medicinal Chemistry Letters; vol. 23, No. 24; Oct. 29, 2013; ISSN: 0960-894X; pp. 6737-6742.

* cited by examiner

*Primary Examiner* — James H Alstrum-Acevedo
*Assistant Examiner* — Justin Christopher Sanchez
(74) *Attorney, Agent, or Firm* — NKL Law; Allen Xue

(57) ABSTRACT

An aryl-fused isoselenazole compound contains a tetrazine substituent represented by formulas (I) and/or (II). The compound has an inhibitory activity on TrxR, and has the feature of targeting the TrxR target. Therefore, the compound has a good antitumor effect on tumors, particularly, gliomas. It effectively inhibits the growth of tumor cells both in vivo and in vitro as a drug.

(I)

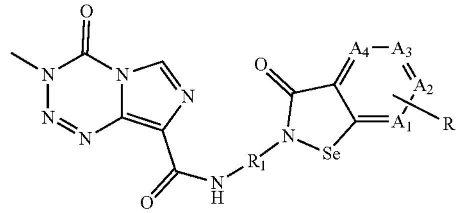

(II)

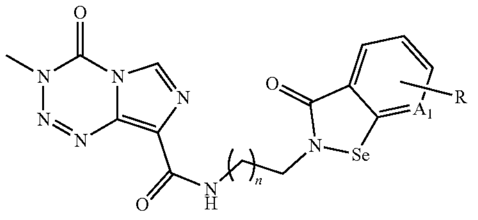

19 Claims, 2 Drawing Sheets

ARYL-FUSED ISOSELENAZOLE COMPOUND CONTAINING TETRAZINE SUBSTITUENT, SYNTHESIS METHOD THEREFOR, AND USE THEREOF

CROSS-REFERENCE TO RELATED APPLICATIONS

This application is a U.S. National stage entry of PCT International application No. PCT/CN2021/086688, filed on Apr. 12, 2021, which claims priority to Chinese Patent Application No. 202010287745.6, entitled "ARYL-FUSED ISOSELENAZOLE COMPOUND CONTAINING TETRAZINE SUBSTITUENT, SYNTHESIS METHOD THEREFOR, AND USE THEREOF," filed with China National Intellectual Property Administration on Apr. 13, 2020, the content of which is incorporated herein by reference in its entirety.

TECHNICAL FIELD

The present disclosure belongs to the field of pharmaceuticals, and specifically relates to a synthesis method for an aryl-fused isoselenazole compound containing a tetrazine substituent, and use thereof for manufacturing a medicament for the treatment of a tumor, particularly brain glioma.

BACKGROUND

Brain glioma is a common in-situ intracranial tumor, accounting for more than 50% of intracranial tumors and 1-3% of malignant tumors of the whole body with respect to the morbidity, and the median overall survival of patients is only 12 to 15 months. Because most of brain gliomas infiltratively grow and have no obvious histological boundary with normal brain tissues, the brain gliomas are very difficult to radically cure by surgical excision. In addition, radiotherapy (RT) is also a treatment method commonly applied in clinical practice, including conventional radiotherapy, three-dimensional conformal radiotherapy, stereotactic radiotherapy, etc. However, because the sensitivity of glioma cells to radiotherapy is not high enough and varies between subtypes, the effect of radiotherapy is difficult to improve, and certain therapeutic effects can be achieved only by combining pharmacotherapy with radiotherapy. Most medicines cannot effectively act on tumor sites due to the existence of the blood-brain barrier, and the killing effect on tumors is limited. As a new-generation alkylating agent, temozolomide (TMZ) can be quickly absorbed after oral administration, and has the characteristics of high efficacy, low toxicity and broad spectrum. Under physiological conditions, TMZ can be ultimately converted into cytotoxic diazomethane, and methylation at the 06 position of guanine leading to cytotoxicity is the main reason for its killing effect. Whether TMZ is used alone or in combination with radiotherapy to treat gliomas, TMZ has a relatively good therapeutic effect. At present, the main clinical protocol of temozolomide is the "stupp" protocol, that is, radiotherapy and adjuvant temozolomide chemotherapy are synchronously conducted. More specifically, the adjuvant TMZ chemotherapy is adopted, one month after the radiotherapy is completed, in cycles of 28 days, in which medication is performed once daily for 5 consecutive days and interrupted for 23 days (150 $mg/m^2/d \times 5$ in cycle 1 and 200 $mg/m^2/d \times 5$ in cycles 2 to 6). The median overall survival of patients treated with the Stupp protocol is 14.6 months, while the median overall survival of patients treated with RT alone was 12.1 months.

Although some achievements have been made, TMZ still has some disadvantages. Firstly, the efficacy is not ideal. Secondly, there are a lot of side effects, leading to adverse effects in patients, such as myelosuppression, gastrointestinal reaction, peripheral neurotoxicity, etc. Thirdly, there is also the problem of drug resistance, that is, 06-methylguanine-DNA methyltransferase (MGMT) can directly cut off the methyl group, making TMZ ineffective. In addition, multidrug resistance (MDR) can also be easily developed. These are the primary causes of the failure of the TMZ chemotherapy for gliomas.

The thioredoxin system (TRX system) includes three parts: reduced nicotinamide adenine dinucleotide phosphate (NADPH), thioredoxin (TRX), and thioredoxin reductase (TrxR), among which TrxR is an NADPH-dependent dimeric selenase containing flavin adenine dinucleotide (FAD) domains. There are three subtypes of mammalian TrxR: TrxR1 in nuclei, TrxR2 in mitochondria and TrxR3 present in the testis. The electron transfer inside the whole TRX system is shown in FIG. 1.

The completely oxidized enzyme accepts electrons from NADPH and then forms a completely reduced enzyme. Finally, the substrate is reduced, in which the C-terminal selenothiol pair plays a role in transferring electrons and is the basis for the redox regulation function of TrxR.

The TRX system can directly resist oxidation and support the functions of other antioxidant enzymes, and can help prevent normal cells from being converted into malignant tumors by preventing exogenous substances or carcinogens from causing oxidative stress. In the aspects of tumor progression and metastasis, the increase in the TrxR/Trx level can promote cell proliferation, resist apoptosis and promote angiogenesis, so the growth of tumors may be promoted.

The TRX system plays an important role in the process of development, progression and metastasis of tumors, and is an important system for maintaining homeostasis and promoting proliferation and angiogenesis in tumor cells.

TrxR is highly expressed in brain tumors, and analysis of clinical data from 433 cases of glioblastoma showed that thioredoxin reductase 1 (TrxR1) was upregulated in more than 66% of cases, which was clearly associated with greater proliferative activity and poorer prognosis. Therefore, it is quite urgent to study the treatment of brain gliomas by aiming at the TrxR target.

SUMMARY

The present disclosure provides an aryl-fused isoselenazole compound containing a tetrazine substituent represented by formula (I) or a pharmaceutically acceptable salt thereof:

(I)

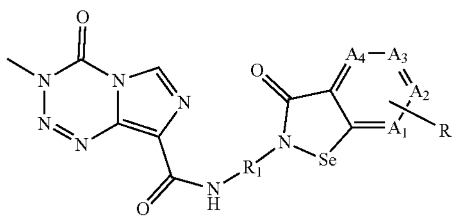

wherein $A_1$, $A_2$, $A_3$ and $A_4$ are identical or different and are independently from each other selected from CH and N, and at most one of which is N; when $A_1$, $A_2$, $A_3$ or $A_4$ is CH, the hydrogen atom therein may be substituted with R, wherein R is selected from hydrogen, cyano, hydroxy, halogen, and nitro, or from amino, sulfhydryl, amido, alkyl, cycloalkyl, alkoxy, heterocyclyl, aryl and heteroaryl, which are substituted with one or more Ra, each Ra is independently from each other selected from hydrogen, cyano, hydroxy, halogen, amino, nitro, sulfhydryl, alkyl, cycloalkyl, alkoxy, aryl, and heteroaryl; $R_1$ is selected from alkylene.

According to an embodiment of the present disclosure, R is selected from hydrogen, cyano, hydroxy, halogen, and nitro, or from amino, sulfhydryl, amido, $C_{1-10}$ alkyl, $C_{3-10}$ cycloalkyl, $C_{1-10}$ alkoxy, 3-10 membered heterocyclyl, $C_{6-14}$ aryl and 5-14 membered heteroaryl, which are substituted with one or more Ra, each Ra is independently from each other selected from hydrogen, cyano, hydroxy, halogen, amino, nitro, sulfhydryl, $C_{1-10}$ alkyl, $C_{3-10}$ cycloalkyl, $C_{1-10}$ alkoxy, 3-10 membered heterocyclyl, $C_{6-14}$ aryl, and 5-14 membered heteroaryl; $R_1$ is selected from $C_{1-10}$ alkylene.

According to an embodiment of the present disclosure, R is selected from hydrogen and halogen, or from $C_{1-6}$ alkyl, $C_{3-6}$ cycloalkyl, $C_{1-6}$ alkoxy, phenyl and pyridyl, which are substituted with one or more Ra, each Ra is independently from each other selected from hydrogen, halogen, $C_{1-6}$ alkyl, $C_{3-6}$ cycloalkyl, $C_{1-6}$ alkoxy, phenyl, and pyridyl; $R_1$ is selected from $C_{1-6}$ alkylene.

According to an embodiment of the present disclosure, R is selected from hydrogen, halogen, $C_{1-6}$ alkyl, and $C_{1-6}$ alkoxy.

According to an embodiment of the present disclosure, R is selected from hydrogen, fluorine, chlorine, bromine, iodine, methyl, ethyl, n-propyl, isopropyl, n-butyl, isobutyl, tert-butyl, n-pentyl, isopentyl, methoxy, ethoxy, n-propoxy, isopropoxy, n-butoxy, isobutoxy, tert-butoxy, n-pentoxy, and isopentoxy.

Preferably, the structure of the aryl-fused isoselenazole compound containing a tetrazine substituent is represented by formula (II):

(II)

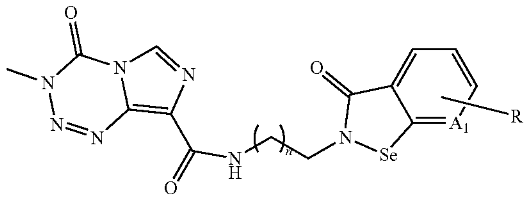

wherein $A_1$ is selected from CH and N; n is 1, 2, 3, 4, 5, or 6; R has the definition described above.

According to an embodiment of the present disclosure, R is selected from hydrogen, halogen, $C_{1-6}$ alkyl, and $C_{1-6}$ alkoxy.

According to an embodiment of the present disclosure, R is selected from hydrogen, fluorine, chlorine, bromine, iodine, methyl, ethyl, n-propyl, isopropyl, n-butyl, isobutyl, tert-butyl, n-pentyl, isopentyl, methoxy, ethoxy, n-propoxy, isopropoxy, n-butoxy, isobutoxy, tert-butoxy, n-pentoxy, and isopentoxy.

Preferably, the aryl-fused isoselenazole compound containing a tetrazine substituent is selected from the compounds in Table 1 below:

TABLE 1

Aryl-fused isoselenazole compounds containing a tetrazine substituent of the present disclosure

| No. | Name | Structure |
|---|---|---|
| 1 | 3,4-dihydro-3-methyl-4-oxo-N-(3(2H)-oxo-1,2-benzisoselenazol-2-yl)-ethyl-imidazo[5,1-d]-1,2,3,5-tetrazine-8-carboxamide | 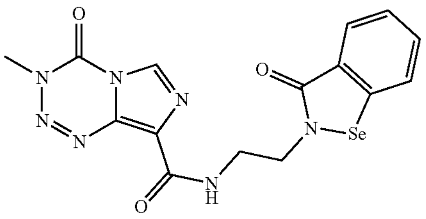 [SMILES: Cn1nnc2c(C(=O)NCCn3[se]c4ccccc4c3=O)ncn2c1=O] |
| 2 | 3,4-dihydro-3-methyl-4-oxo-N-(3(2H)-oxo-5-fluoro-1,2-benzisoselenazol-2-yl)-ethyl-imidazo[5,1-d]-1,2,3,5-tetrazine-8-carboxamide | 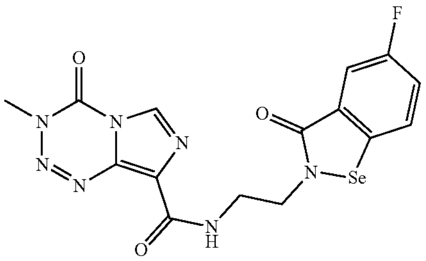 [SMILES: Cn1nnc2c(C(=O)NCCn3[se]c4ccc(F)cc4c3=O)ncn2c1=O] |

TABLE 1-continued

| No. | Name | Structure |
| --- | --- | --- |
| | Aryl-fused isoselenazole compounds containing a tetrazine substituent of the present disclosure | |
| 3 | 3,4-dihydro-3-methyl-4-oxo-N-(3(2H)-oxo-6-fluoro-1,2-benzisoselenazol-2-yl)-ethyl-imidazo[5,1-d]-1,2,3,5-tetrazine-8-carboxamide | 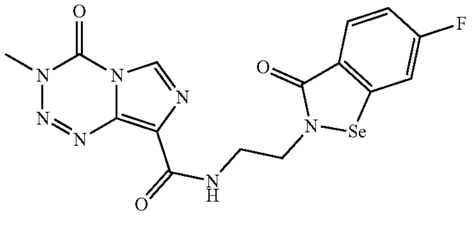 [SMILES: Cn1nnc2c(C(=O)NCCn3[se]c4cc(F)ccc4c3=O)ncn2c1=O] |
| 4 | 3,4-dihydro-3-methyl-4-oxo-N-(3(2H)-oxo-5-chloro-1,2-benzisoselenazol-2-yl)-ethyl-imidazo[5,1-d]-1,2,3,5-tetrazine-8-carboxamide | 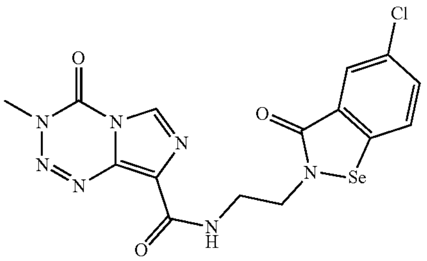 [SMILES: Cn1nnc2c(C(=O)NCCn3[se]c4ccc(Cl)cc4c3=O)ncn2c1=O] |
| 5 | 3,4-dihydro-3-methyl-4-oxo-N-(3(2H)-oxo-5-bromo-1,2-benzisoselenazol-2-yl)-ethyl-imidazo[5,1-d]-1,2,3,5-tetrazine-8-carboxamide | 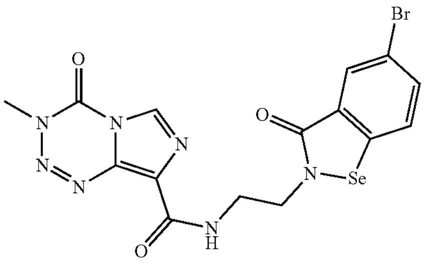 [SMILES: Cn1nnc2c(C(=O)NCCn3[se]c4ccc(Br)cc4c3=O)ncn2c1=O] |
| 6 | 3,4-dihydro-3-methyl-4-oxo-N-(3(2H)-oxo-5-methyl-1,2-benzisoselenazol-2-yl)-ethyl-imidazo[5,1-d]-1,2,3,5-tetrazine-8-carboxamide | 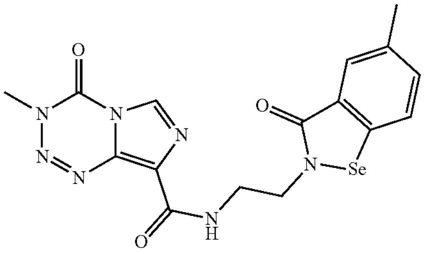 [SMILES: Cc1ccc2[se]n(CCNC(=O)c3ncn4c(=O)n(C)nnc34)c(=O)c2c1] |
| 7 | 3,4-dihydro-3-methyl-4-oxo-N-(3(2H)-oxo-5-methoxy-1,2-benzisoselenazol-2-yl)-ethyl-imidazo[5,1-d]-1,2,3,5-tetrazine-8-carboxamide | 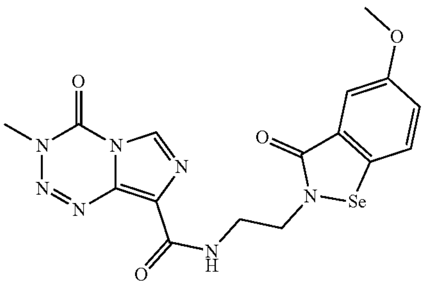 [SMILES: COc1ccc2[se]n(CCNC(=O)c3ncn4c(=O)n(C)nnc34)c(=O)c2c1] |

TABLE 1-continued

Aryl-fused isoselenazole compounds containing a tetrazine substituent of the present disclosure

| No. | Name | Structure |
| --- | --- | --- |
| 8 | 3,4-dihydro-3-methyl-4-oxo-N-(3(2H)-oxo-6-methyl-1,2-benzisoselenazol-2-yl)-ethyl-imidazo[5,1-d]-1,2,3,5-tetrazine-8-carboxamide | 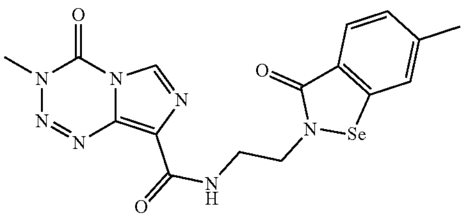 |

According to an embodiment of the present disclosure, the pharmaceutically acceptable salt of the compound represented by formula (I) or formula (II) includes: an acid addition salt formed from the compound and an inorganic or organic acid; the inorganic acid is selected from at least one of hydrochloric acid, hydrofluoric acid, hydrobromic acid, hydroiodic acid, perchloric acid, sulfuric acid, pyrosulfuric acid, phosphoric acid, and nitric acid; the organic acid is selected from at least one of formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptonic acid, glycerophosphoric acid, aspartic acid, sulfosalicylic acid, hemisulfuric acid, and thiocyanic acid;

alternatively, the pharmaceutically acceptable salt of the compound represented by formula (I) or formula (II) is an alkali metal salt, alkaline earth metal salt or ammonium salt of the compound, or a salt formed from the compound and an organic base providing physiologically acceptable cations, e.g., a salt formed from the compound and at least one of the following substances: sodium ion, potassium ion, calcium ion, magnesium ion, morpholine, piperidine, triethylamine, tripropylamine, tributylamine, diisopropylamine, diisopropylethylenediamine, pyridine, dimethylamine, diethylamine, N-methylglucamine, dimethylglucamine, ethylglucamine, lysine, dicyclohexylamine, 1,6-hexanediamine, ethanolamine, glucosamine, meglumine, sarcosine, serinol, trihydroxymethylaminomethane, aminopropanediol, and 1-amino-2,3,4-butanetriol.

The present disclosure further provides a preparation method for the compound represented by formula (I), which comprises the following steps:

1) diazotizing an amino group in a compound A, followed by reacting with $Na_2Se_2$ to prepare a compound B:

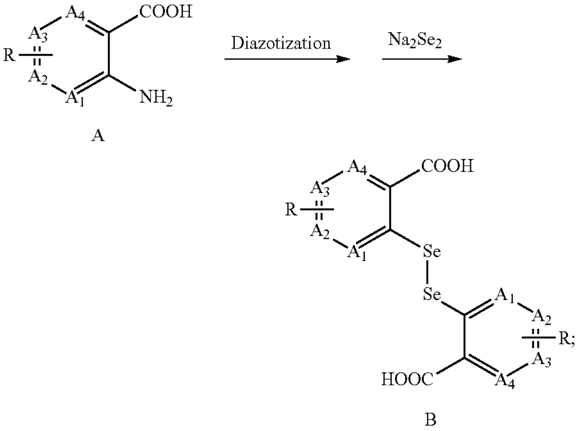

A

B wherein $A_1$, $A_2$, $A_3$, $A_4$, R and $R_1$ have the definitions described above;

2) reacting the compound B with thionyl chloride to prepare a compound C:

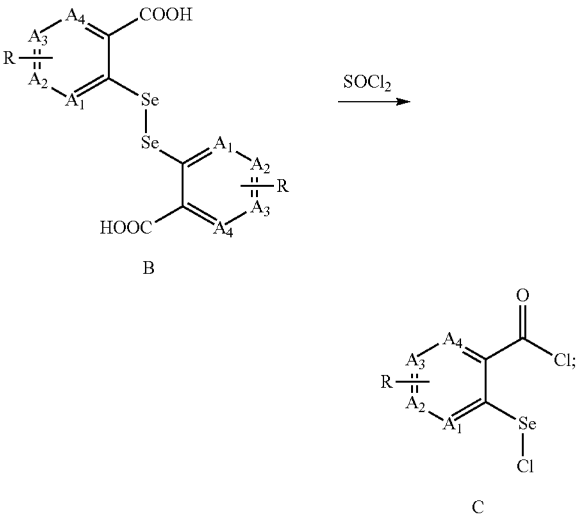

B

C 3) reacting the compound C with $H_2N—R_1—NHBoc$ to prepare a compound D:

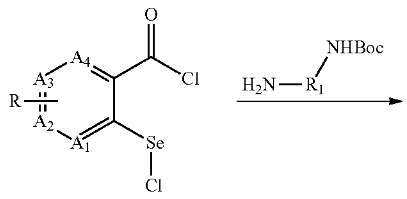

C

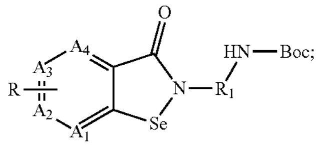

D wherein Boc represents tert-butyloxycarbonyl;

4) deprotection of the Boc protective group of the compound D in the presence of an acid to prepare a compound E:

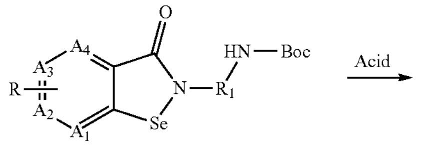

D

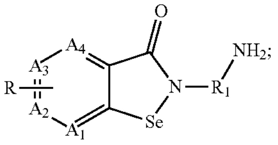

E and 5) reacting the compound E with a compound F to prepare the compound represented by formula (I):

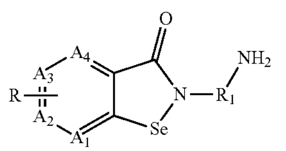

E

+

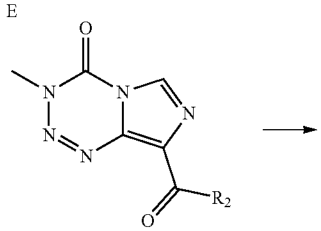

F

-continued

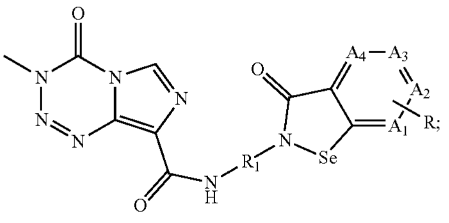

F wherein in the compound F, $R_2$ is selected from chlorine, bromine, hydroxy, and $—OR_3$, wherein $R_3$ is selected from $C_{1-6}$ alkyl, succinimidyl, tert-butyloxycarbonyl, methylsulfonyl, p-nitrobenzenesulfonyl, p-toluenesulfonyl, and isobutyloxycarbonyl.

According to an embodiment of the present disclosure, $Na_2Se_2$ in step 1) can be prepared from elemental selenium and sodium hydrosulfite.

According to an embodiment of the present disclosure, step 2) may be carried out in the presence of a catalytic amount of DMIF. According to an embodiment of the present disclosure, the acid in step 4) may be hydrochloric acid. Further, step 4) may be carried out in an organic solvent such as ethyl acetate.

According to an embodiment of the present disclosure, the compound F is commercially available or may be obtained by using a conventional method in the art or prepared through the following steps:

a) allowing compound TMZ (i.e. temozolomide) to react under the action of sulfuric acid and sodium nitrite to give a compound F-1:

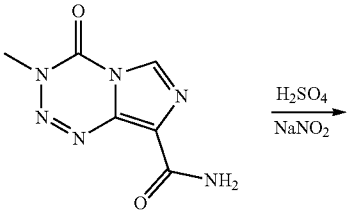

TMZ

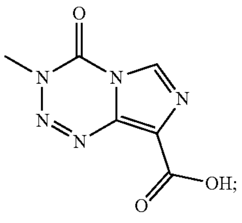

F-1 and optional step b): reacting the compound F-1 with thionyl chloride or dibromosulfoxide in the presence of a catalytic amount of DMF to give a compound F-2:

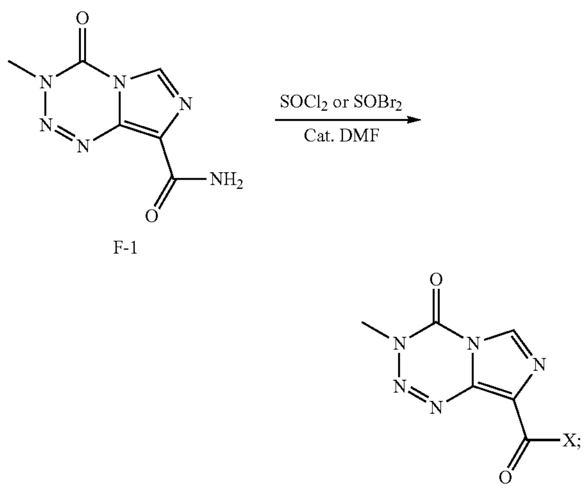

F-1

F-2
wherein X is Cl or Br or optional step c): allowing the compound F-1 to further react to give the compound F in which $R_2$ is —$OR_3$, wherein $R_3$ is $C_{1-6}$ alkyl, succinimidyl, tert-butoxycarbonyl, methanesulfonyl, p-nitrobenzenesulfonyl, p-toluenesulfonyl, or isobutyloxycarbonyl.

Step c) is selected from step c-1), step c-2), step c-3), step c-4) and step c-5) below:

step c-1): reacting the compound F-1 with $R_4OH$ under the action of an acid to give a compound F-3 (i.e. the compound F in which $R_2$ is —$OR_3$ and $R_3$ is $C_{1-6}$ alkyl):

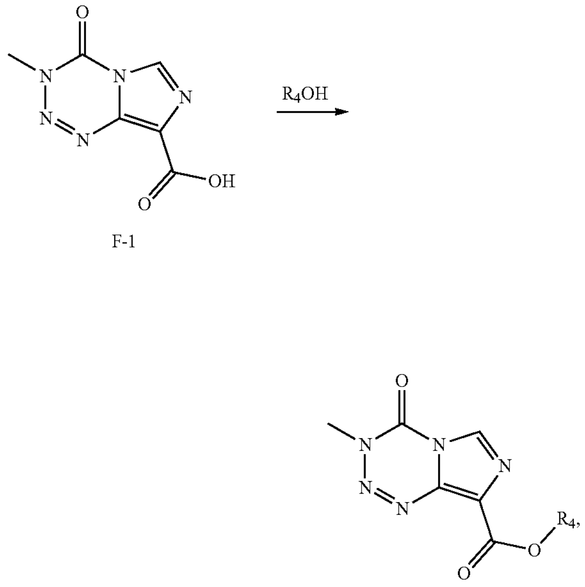

F-1

F-3 wherein $R_4$ is $C_{1-6}$ alkyl;

step c-2): reacting the compound F-1 with $R_5Cl$ under the action of a base to give a compound F-4 (i.e. the compound F in which $R_2$ is —$OR_3$ and $R_3$ is methanesulfonyl, p-nitrobenzenesulfonyl or p-toluenesulfonyl):

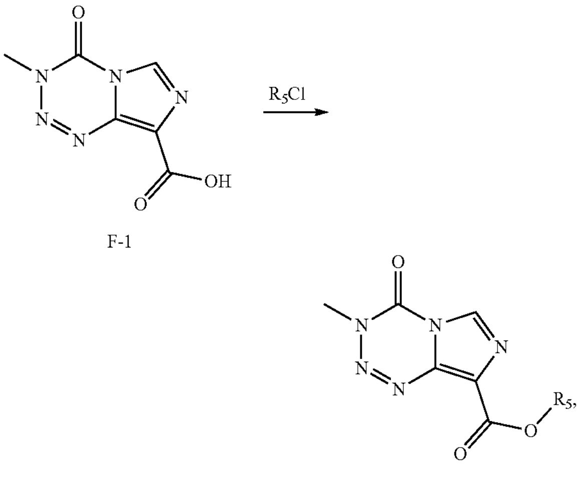

F-1

F-4 wherein $R_5$ is methylsulfonyl, p-nitrobenzenesulfonyl or p-toluenesulfonyl;

step c-3): reacting the compound F-1 with N-hydroxysuccinimide to give a compound F-5 (i.e. the compound F in which $R_2$ is —$OR_3$ and $R_3$ is succinimidyl):

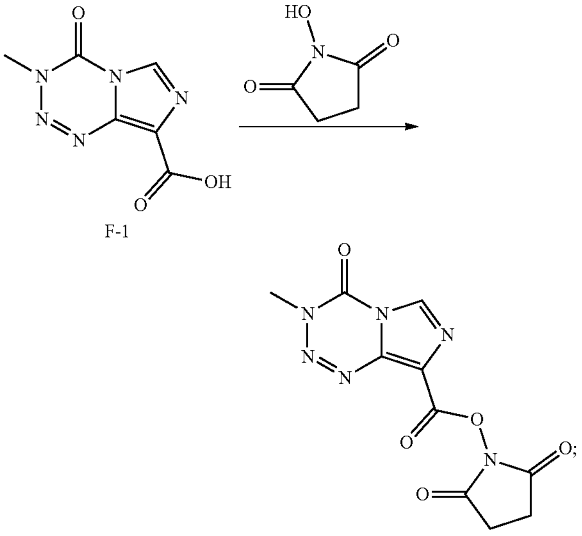

F-1

F-5 step c-4): reacting the compound F-1 with di-tert-butyl dicarbonate to give a compound F-6 (i.e. the compound F in which $R_2$ is —$OR_3$ and $R_3$ is tert-butoxycarbonyl):

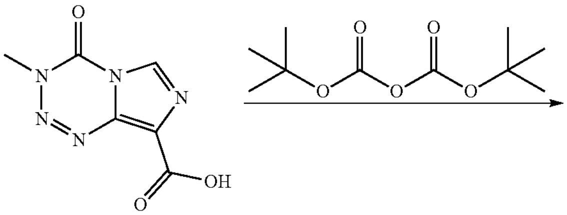

F-1

-continued

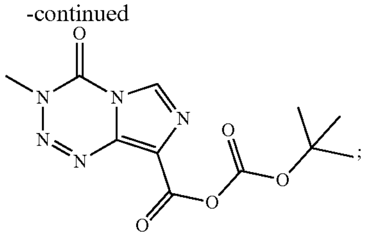

F-6 step c-5): reacting the compound F-1 with isobutyl chloroformate to give a compound F-7 (i.e. the compound F in which $R_2$ is —$OR_3$ and $R_3$ is isobutyloxycarbonyl):

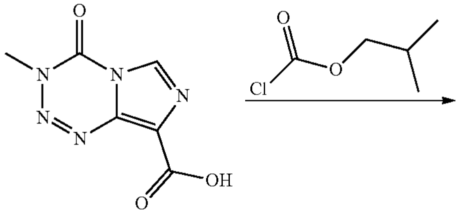

F-1

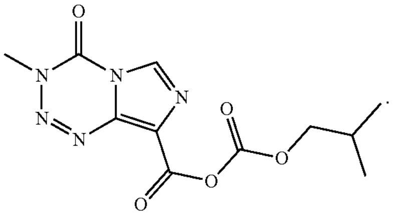

F-7

The present disclosure further provides a pharmaceutical composition, which comprises the aryl-fused isoselenazole compound represented by formula (I) containing a tetrazine substituent or the pharmaceutically acceptable salt thereof, and a pharmaceutically acceptable carrier.

According to an embodiment of the present disclosure, the pharmaceutical composition is suitable for enteral, topical or parenteral administration, e.g., oral administration, injection, implantation, topical application, spray, inhalation, or other routes of administration.

According to an embodiment of the present disclosure, the oral pharmaceutical composition may be any one of a tablet, a capsule, a pill, an oral liquid preparation, granules, an injection, a topical preparation, and a powder.

The tablet may be a common tablet, a buccal tablet, a sublingual tablet, a buccal patch, a chewable tablet, a dispersible tablet, a soluble tablet, an effervescent tablet, a vaginal tablet, a vaginal effervescent tablet, a sustained-release tablet, a controlled-release tablet, an enteric-coated tablet, or a buccal immediate-release tablet; the capsule may be a hard capsule, a soft capsule, a sustained-release capsule, a controlled-release capsule, or an enteric-coated capsule; the pill includes a dripping pill, a sugar pill, or a pellet; the oral liquid preparation may be a syrup, a suspension, an oral solution, an oral suspension, an oral emulsion, a syrup, a mixture, a distillate, or a liniment; the granules may be suspension granules, effervescent granules, enteric-coated granules, sustained-release granules, or controlled-release granules. The injection may be any one of an injectable liquid, a sterile powder or sterile block for injection, and a concentrated solution for transfusion and injection. The topical preparation may be any one of a suppository, an aerosol, an inhalation powder, a spray, a film, a gel, a patch, a colloid, an emplastrum, a plaster, an ointment, a liniment, a lotion, an application agent, and a gelatin.

According to an embodiment of the present disclosure, the pharmaceutical composition may be prepared by adopting a preparation technique means well-known in the art.

According to an embodiment of the present disclosure, the pharmaceutical composition may be an inclusion preparation or a dispersion preparation.

According to an embodiment of the present disclosure, the pharmaceutically acceptable carrier is a common excipient or auxiliary material well-known in the art for manufacturing the preparation described above, wherein the common excipient or auxiliary material for oral or topical preparations includes, but is not limited to, a filler, a diluent, a lubricant, a glidant, an antiadherent, a dispersant, a wetting agent, a binder, a regulator, a solubilizer, an antioxidant, a bacteriostat, an emulsifier, etc.

The binder is, for example, syrup, acacia, gelatin, sorbitol, tragacanth, cellulose or a derivative thereof, gelatin paste, syrup, starch paste, or polyvinylpyrrolidone, a preferred cellulose derivative being microcrystalline cellulose, sodium carboxymethylcellulose, ethylcellulose, or hydroxypropylmethylcellulose; the filler is, for example, lactose, powdered sugar, dextrin, starch or a derivative thereof, cellulose or a derivative thereof, an inorganic calcium salt, sorbitol, or glycine, the inorganic calcium salt is preferably calcium sulphate, calcium phosphate, dicalcium phosphate, or precipitated calcium carbonate; the lubricant is, for example, colloidal silicon dioxide, magnesium stearate, talc, aluminum hydroxide, boric acid, hydrogenated vegetable oil, or polyethylene glycol; the disintegrant is, for example, starch or a derivative thereof, polyvinylpyrrolidone, or microcrystalline cellulose, the starch derivative being preferably sodium carboxymethyl starch, sodium starch glycolate, pregelatinized starch, modified starch, hydroxypropyl starch, or corn starch; the wetting agent is, for example, sodium dodecyl sulfate, water, or an alcohol; the excipient is preferably α-cyclodextrin, β-cyclodextrin, γ-cyclodextrin, Celadon102CG, povidone (PVP)-K series (including povidone K30 (PVPK30)), talc, magnesium stearate, or ethanol, etc.

According to an embodiment of the present disclosure, the common excipient or auxiliary material for the injection includes: an antioxidant, a bacteriostat, a pH regulator, an emulsifier, or a solubilizer.

The antioxidant includes sodium thiosulfate, sodium sulfite, sodium bisulfite, dibutylbenzoic acid, or sodium pyrosulfite; the bacteriostat includes phenol, cresol, or chlorobutanol, preferably 0.5% phenol, 0.3% cresol or 0.5% chlorobutanol; the pH regulator includes hydrochloric acid, citric acid, potassium hydroxide, sodium hydroxide, sodium citrate, sodium dihydrogen phosphate, or disodium hydrogen phosphate; the emulsifier includes polysorbate-80, sorbitan fatty acid, pluronic F-68, lecithin, or soybean phospholipid; the solubilizer includes Tween-80 or glycerol.

According to an embodiment of the present disclosure, the compound represented by formula (I) or the pharmaceutically acceptable salt thereof and the pharmaceutically acceptable sustained/controlled-release carrier may also be prepared into a sustained/controlled-release preparation according to a conventional preparation method for sustained/controlled-release preparations. For example, the compound represented by formula (I) or the pharmaceutically acceptable salt thereof may be coated with a retardant or microencapsulated and then prepared into pellets, such as sustained-release pellets or controlled-release pellets.

The sustained/controlled-release carrier includes, but is not limited to, a greasy additive, a hydrophilic colloid, or a coating retardant; the greasy additive includes glyceryl monostearate, hydrogenated castor oil, mineral oil, polysiloxane, or dimethyl siloxane; the hydrophilic colloid includes sodium carboxymethylcellulose, hydroxypropylcellulose, hydroxypropyl methylcellulose, polyvinylpyrrolidone (PVP), acacia, tragacanth, or carbopol; the coating retardant includes ethyl cellulose (EC), hydroxypropyl methylcellulose (HPMC), polyvinylpyrrolidone (PVP), cellulose acetate phthalate (CAP), or an acrylic resin.

In a preferred embodiment of the present disclosure, the pharmaceutical composition comprises about 1-99 wt % of any one or a combination of the compound represented by formula (I) and the pharmaceutically acceptable salt thereof and 1-99 wt % of the pharmaceutically acceptable carrier, depending on a desired route of administration.

The present disclosure further provides use of the compound represented by formula (I) or the pharmaceutically acceptable salt thereof or the pharmaceutical composition comprising the same for inhibiting the activity of thioredoxin reductase (TrxR) or manufacturing a thioredoxin reductase (TrxR) inhibitor.

The present disclosure further provides use of the compound represented by formula (I) or the pharmaceutically acceptable salt thereof or the pharmaceutical composition comprising the same for treating or alleviating a disease or condition associated with upregulated expression or increased activity of TrxR or for manufacturing a medicament for the treatment or alleviation of a disease or condition associated with upregulated expression or increased activity of TrxR.

The present disclosure further provides use of the compound represented by formula (I) or the pharmaceutically acceptable salt thereof or the pharmaceutical composition comprising the same for treating tumors or manufacturing a medicament for the treatment of a tumor.

The present disclosure further provides a compound represented by formula (I) or a pharmaceutically acceptable salt thereof or a pharmaceutical composition comprising the same for inhibiting the activity of thioredoxin reductase (TrxR), for treating or alleviating a disease or condition associated with upregulated expression or increased activity of TrxR, for treating a tumor, for use in a method for treating a tumor, or for manufacturing a medicament for the treatment of a tumor.

The present disclosure further provides a method for treating or alleviating a disease or condition associated with upregulated expression or increased activity of TrxR in a subject, which comprises administering to the subject in need thereof a therapeutically effective amount of a compound represented by formula (I) or a pharmaceutically acceptable salt thereof or a pharmaceutical composition comprising the same.

The present disclosure further provides a method for treating a tumor in a subject, which comprises administering to the subject in need thereof a therapeutically effective amount of a compound represented by formula (I) or a pharmaceutically acceptable salt thereof or a pharmaceutical composition comprising the same.

According to an embodiment of the present disclosure, the disease or condition associated with upregulated expression or increased activity of TrxR is a tumor, including but not limited to, any one of brain glioma, lung cancer, liver cancer, blood cancer, bone cancer, pancreatic cancer, skin cancer, melanoma, uterine cancer, ovarian cancer, rectal cancer, gastric cancer, colon cancer, breast cancer, uterine cancer, fallopian tube cancer, endometrial cancer, cervical cancer, vaginal cancer, vulval cancer, esophageal cancer, small intestine cancer, endocrine system cancer, soft tissue sarcoma, urethral cancer, prostate cancer, lymphocytoma, bladder cancer, kidney cancer, ureter cancer, spinal tumor, brain stem glioma, pituitary adenoma, lung cancer, liver cancer, and blood cancer, and the tumor is preferably brain glioma.

Beneficial Effects

The aryl-fused isoselenazole compound containing a tetrazine substituent according to the present disclosure has the characteristic of targeting the TrxR target, and TrxR has the characteristic of a tumor growth marker because TrxR is a tumor growth-regulating enzyme. In addition, TrxRs in brain glioma are multiple recognized highly expressed tumor markers, so the compound aiming at the inhibition of targeted TrxR would have a good anti-tumor effect against brain gliomas. At present, the compound can well inhibit the growth of each brain glioma cell line both in vivo and in vitro.

DEFINITIONS AND DESCRIPTION

Figure 1:
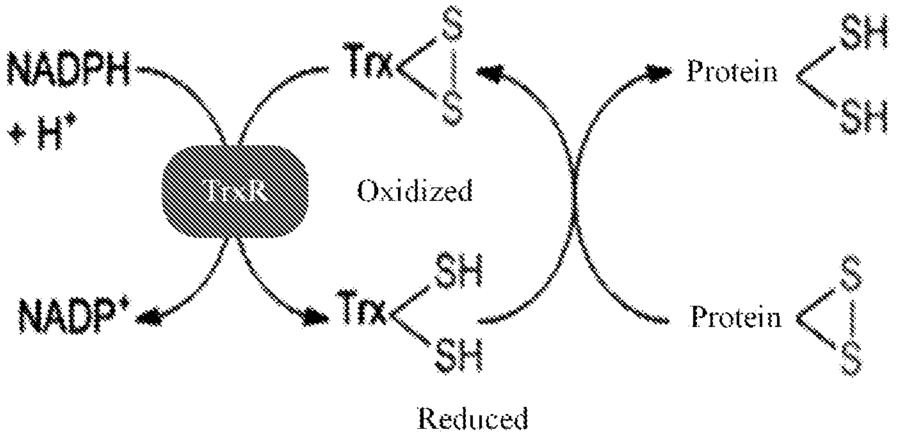
FIG. 1 is a schematic diagram of electron transfer within a TRX system.

The term "alkyl" refers to a linear or branched saturated monovalent hydrocarbon group having 1 to 12 carbon atoms. For example, "$C_{1-10}$ alkyl" refers to linear and branched alkyl groups having 1, 2, 3, 4, 5, 6, 7, 8, 9 or 10 carbon atoms. The alkyl is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl, etc., or isomers thereof.

The term "alkoxy" refers to —O—$C_{1-10}$ alkyl, wherein $C_{1-10}$ alkyl has the definition described above.

The term "cycloalkyl" refers to a saturated monovalent monocyclic or bicyclic hydrocarbon ring having 3 to 20 carbon atoms. The term "$C_{3-10}$ cycloalkyl" refers to a saturated monovalent monocyclic or bicyclic hydrocarbon ring having 3, 4, 5, 6, 7, 8, 9 or 10 carbon atoms. The $C_{3-10}$ cycloalkyl may be a monocyclic hydrocarbon group, such as cyclopropyl, cyclobutyl, cyclopentyl, cyclohexyl, cycloheptyl, cyclooctyl, cyclononyl or cyclodecyl, or a bicyclic hydrocarbon group, such as a decaline ring.

As used herein, "alkylene" refers to a divalent alkyl group; for example, $C_{1-10}$ alkylene refers to a divalent $C_{1-10}$ alkyl group.

The term "heterocyclyl" refers to a saturated monovalent monocyclic or bicyclic hydrocarbon ring containing 3 to 20 atoms, which contains 1 to 5 heteroatoms independently selected from N, O and S, and is preferably "3-10 membered heterocyclyl". The term "3-10 membered heterocyclyl" refers to a saturated monovalent monocyclic or bicyclic hydrocarbon ring containing 1 to 5 (preferably 1 to 3) heteroatoms selected from N, O and S. The heterocyclyl may be connected to the rest of the molecule through any of the carbon atoms or the nitrogen atom(s) (if present). In particular, the heterocyclyl may include, but is not limited to: 4-membered rings such as azetidinyl and oxetanyl; 5-membered rings such as tetrahydrofuranyl, dioxolyl, pyrrolidinyl, imidazolidinyl, pyrazolidinyl and pyrrolinyl; 6-membered rings such as tetrahydropyranyl, piperidyl, morpholinyl, dithianyl, thiomorpholinyl, piperazinyl and trithianyl; or 7-membered rings such as diazepanyl. Optionally, the heterocyclyl may be benzo-fused. The heterocyclyl may be bicyclic, for example, but not limited to, a 5,5-membered ring such as a hexahydrocyclopenta[c]pyrrol-2(1H)-yl ring, or a 5,6-membered bicyclic ring such as a hexahydropyrrolo[1,2-a]pyrazin-2(1H)-yl ring. The ring containing nitrogen atoms may be partially unsaturated, i.e., it may contain one or more double bonds, for example, but not limited to, 2,5-dihydro-1H-pyrrolyl, 4H-[1,3,4]thiadiazinyl, 4,5-dihydrooxazolyl or 4H-[1,4]thiazinyl, or it may be benzo-fused, for example, but not limited to, dihydroisoquinolyl. According to the present disclosure, the heterocyclyl is non-aromatic.

The term "aryl" refers to a monovalent aromatic or partially aromatic monocyclic, bicyclic or tricyclic hydrocarbon ring having 6 to 20 carbon atoms (preferably 6 to 14 carbon atoms), and preferably to "$C_{6-14}$ aryl". The term "$C_{6-10}$ aryl" preferably refers to an aromatic or partially aromatic monovalent monocyclic, bicyclic or tricyclic hydrocarbon ring having 6, 7, 8, 9, 10, 11, 12, 13 or 14 carbon atoms ("$C_{6-14}$ aryl"), in particular a ring having 6 carbon atoms ("$C_6$ aryl"), such as phenyl or biphenyl, a ring having 9 carbon atoms ("$C_9$ aryl"), such as indanyl or indenyl, a ring having 10 carbon atoms ("$C_{10}$ aryl"), such as tetrahydronaphthyl, dihydronaphthyl or naphthyl, a ring having 13 carbon atoms ("$C_{13}$ aryl"), such as fluorenyl, or a ring having 14 carbon atoms ("$C_{14}$ aryl"), such as anthryl. When the $C_{6-14}$ aryl is substituted, it may be monosubstituted or polysubstituted. In addition, the substitution site is not limited, and may be, for example, ortho-substitution, para-substitution, or meta-substitution.

The term "heteroaryl" refers to a monovalent monocyclic, bicyclic or tricyclic aromatic ring group having 3 to 20 ring atoms and containing 1 to 5 heteroatoms independently selected from N, O and S, such as "5-14 membered heteroaryl". The term "5-14 membered heteroaryl" refers to a monovalent monocyclic, bicyclic or tricyclic aromatic ring group having 5, 6, 7, 8, 9, 10, 11, 12, 13 or 14 ring atoms (in particular 5 or 6 or 9 or 10 carbon atoms) and containing 1 to 5 (preferably 1 to 3) heteroatoms independently selected from N, O and S, and may be benzo-fused in each case. In particular, the heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl and the like and benzo derivatives thereof, such as benzofuranyl, benzothienyl, benzoxazolyl, benzoisoxazolyl, benzimidazolyl, benzotriazolyl, indazolyl, indolyl, isoindolyl and the like; or pyridyl, pyridazinyl, pyrimidinyl, pyrazinyl, triazinyl and the like and benzo derivatives thereof, such as quinolyl, quinazolinyl, isoquinolyl and the like; or azocinyl, indolizinyl, purinyl and the like and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl and the like.

The term "amido" refers to a Ra—C(═O)—NH— group, wherein Ra has the definition described above.

DETAILED DESCRIPTION

The technical solutions of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared by known methods.

Example 1

3,4-dihydro-3-methyl-4-oxo-N-(3(2H)-oxo-1,2-benzisoselenazol-2-yl)-ethyl-imidazo[5,1-d]-1,2,3,5-tetrazine-8-carboxamide (No. 1)

1) To a beaker was added 28 g of 2-aminobenzoic acid, followed by a mixed liquid of 40 mL of concentrated hydrochloric acid and 40 mL of water. The mixture was cooled in an ice bath to keep the reaction temperature at below 5° C. A solution of $NaNO_2$ (18 g dissolved in 40 mL of water) was slowly added dropwise. After completion of the addition dropwise, the mixture was reacted for another 2 h to give a diazonium salt solution for later use. 16 g of NaOH was added to 100 mL of water and dissolved by stirring at 50° C., and then 17.6 g of sodium hydrosulfite was added in small batches. After the mixture became clear, 16 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 2,2'-diselanediyldibenzoic acid (25 g, 63%).

2) To 2,2'-diselanediyldibenzoic acid (4 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 2-selenochlorobenzoyl chloride (3 g, 59%).

3) Boc-ethylenediamine (1.60 g, 10 mmol) was dissolved in dichloromethane (10 mL), and 1.39 mL of triethylamine was added. A solution of 2-selenochlorobenzoyl chloride (2.54 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-1,2-benzisoselenazol-2-yl)-ethyl-1-carbamate (1.4 g, 41%).

4) To a 50 mL single-neck flask was added tert-butyl (3(2H)-oxo-1,2-benzisoselenazol-2-yl)-ethyl-1-carbamate (0.500 g, 1.47 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-aminoethyl-[1,2-benzisoselenazol-3(2H)-one]hydrochloride (0.405 g, 90%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 75%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-Aminoethyl-[1,2-benzisoselenazol-3(2H)-one]hydrochloride (0.611 g, 2.2 mmol) was reacted with 1 mL of triethylamine in dichloromethane for 1 h first, and a solution of 3,4-dihydro-3-methyl-4-oxo-imidazo[5,1-d]-1,2,3,5-tetrazine-8-carbonyl chloride (0.363 g, 1.7 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a yellow solid (441 mg, 62%). $^1H$ NMR (400 MHz, DMSO-$d_6$) δ 8.84 (s, 1H), 8.67 (s, 1H), 8.04 (d, J=7.9 Hz, 1H), 7.82 (d, J=7.5 Hz, 1H), 7.59 (t, J=7.2 Hz, 1H), 7.40 (t, J=7.2 Hz, 1H), 3.94 (s, 2H), 3.86 (s, 3H), 3.66-3.56 (m, 2H). $^{13}C$ NMR (101 MHz, DMSO-$d_6$) δ 166.55, 159.92, 139.62, 139.11, 134.44, 131.37, 130.19, 128.43, 127.73, 127.27, 125.85, 125.64, 42.75, 39.41, 36.13.

Example 2

3,4-dihydro-3-methyl-4-oxo-N-(3(2H)-oxo-5-fluoro-1,2-benzisoselenazol-2-yl)-ethyl-imidazo[5,1-d]-1,2,3,5-tetrazine-8-carboxamide (No. 2)

1) To a beaker was added 7.75 g of 2-amino-5-fluorobenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 2 to 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 5,5'-difluoro-2,2'-diselanediyldibenzoic acid (6 g, 55%).

2) To 5,5'-difluoro-2,2'-diselanediyldibenzoic acid (4.36 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 5-fluoro-2-selenochlorobenzoyl chloride (3.25 g, 60%).

3) Boc-ethylenediamine (1.60 g, 10 mmol) was dissolved in dichloromethane (10 mL), and 1.39 mL of triethylamine was added. A solution of 5-fluoro-2-selenochlorobenzoyl chloride (2.72 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-5-fluoro-1,2-benzisoselenazol-2-yl)-ethyl-1-carbamate (1.22 g, 34%).

4) To a 25 mL single-neck flask was added tert-butyl (3(2H)-oxo-5-fluoro-1,2-benzisoselenazol-2-yl)-ethyl-1-carbamate (0.359 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-5-fluoro-1,2-benzisoselenazol-3(2H)-one hydrochloride (0.251 g, 85%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 75%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%). 7) 2-(2-Aminoethyl)-5-fluoro-1,2-benzisoselenazol-3(2H)-one hydrochloride (222 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (50 mg, 23%). $^{1}$H NMR (400 MHz, DMSO-$d_6$) δ 8.84 (s, 1H), 8.67 (s, 1H), 8.04 (dd, J=8.6, 4.9 Hz, 1H), 7.63-7.44 (m, 2H), 3.94 (t, J=5.4 Hz, 2H), 3.86 (s, 3H), 3.66-3.55 (m, 2H). $^{13}$C NMR (101 MHz, DMSO-$d_6$) δ 165.62, 165.59, 162.25, 159.95, 159.84, 139.13, 134.61, 134.46, 130.17, 129.40, 129.33, 128.46, 127.88, 127.81, 119.63, 119.39, 113.07, 112.84, 43.01, 38.98, 36.15.

Example 3

3,4-dihydro-3-methyl-4-oxo-N-(3(2H)-oxo-6-fluoro-1,2-benzisoselenazol-2-yl)-ethyl-imidazo[5,1-d]-1,2,3,5-tetrazine-8-carboxamide (No. 3)

1) To a beaker was added 7.75 g of 2-amino-6-fluorobenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 4,4'-difluoro-2,2'-diselanediyldibenzoic acid (5.5 g, 50%).

2) To 4,4'-difluoro-2,2'-diselanediyldibenzoic acid (4.36 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 4-fluoro-2-selenochlorobenzoyl chloride (3.00 g, 55%).

3) Boc-ethylenediamine (1.60 g, 10 mmol) was dissolved in dichloromethane (10 mL), and 1.39 mL of triethylamine was added. A solution of 4-fluoro-2-selenochlorobenzoyl chloride (2.72 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-6-fluoro-1,2-benzisoselenazol-2-yl)-ethyl-1-carbamate (1.07 g, 30%).

4) To a 25 mL single-neck flask was added tert-butyl (3(2H)-oxo-6-fluoro-1,2-benzisoselenazol-2-yl)-ethyl-1-carbamate (0.359 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-6-fluoro-1,2-benzisoselenazol-3(2H)-one hydrochloride (0.275 g, 93%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 80%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-6-fluoro-1,2-benzisoselenazol-3(2H)-one hydrochloride (222 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (120 mg, 55%). $^{1}$H NMR (400 MHz, DMSO-$d_6$) δ 8.84 (s, 1H), 8.68 (t, J=5.5 Hz, 1H), 7.82 (ddd, J=16.4, 8.8, 3.8 Hz, 2H), 7.26 (td, J=8.7, 2.1 Hz, 1H), 3.93 (t, J=5.7 Hz, 2H), 3.86 (s, 3H), 3.64-3.53 (m, 2H). $^{13}$C NMR (101 MHz, DMSO-$d_6$) δ 165.71, 165.25, 162.77, 160.01, 141.75, 141.65, 139.17, 134.50, 130.18, 129.49, 129.40, 128.50, 124.55, 114.16, 113.92, 112.45, 112.18, 42.85, 38.97, 36.19.

Example 4

3,4-dihydro-3-methyl-4-oxo-N-(3(2H)-oxo-5-chloro-1,2-benzisoselenazol-2-yl)-ethyl-imidazo[5,1-d]-1,2,3,5-tetrazine-8-carboxamide (No. 4)

1) To a beaker was added 8.85 g of 2-amino-5-chlorobenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 5,5'-dichloro-2,2'-diselanediyldibenzoic acid (5.98 g, 51%).

2) To 5,5'-dichloro-2,2'-diselanediyldibenzoic acid (4.69 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 5-chloro-2-selenochlorobenzoyl chloride (3.63 g, 63%).

3) Boc-ethylenediamine (1.60 g, 10 mmol) was dissolved in dichloromethane (10 mL), and 1.39 mL of triethylamine was added. A solution of 5-chloro-2-selenochlorobenzoyl chloride (2.88 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-5-chloro-1,2-benzisoselenazol-2-yl)-ethyl-1-carbamate (1.12 g, 30%).

4) To a 25 mL single-neck flask was added tert-butyl (3(2H)-oxo-5-chloro-1,2-benzisoselenazol-2-yl)-ethyl-1-carbamate (0.375 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-5-chloro-1,2-benzisoselenazol-3(2H)-one hydrochloride (0.284 g, 91%).

5) TMZ (0.93 g, 4.8 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 80%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-5-chloro-1,2-benzisoselenazol-3(2H)-one hydrochloride (234 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (147 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (147 mg, 65%). $^{1}H$ NMR (400 MHz, DMSO-$d_6$) δ 8.84 (s, 1H), 8.67 (t, J=5.1 Hz, 1H), 8.03 (d, J=8.6 Hz, 1H), 7.77 (s, 1H), 7.64 (d, J=8.4 Hz, 1H), 3.94 (t, J=5.3 Hz, 2H), 3.86 (s, 3H), 3.60 (d, J=5.6 Hz, 2H). $^{13}C$ NMR (101 MHz, DMSO-$d_6$) δ 165.35, 159.98, 139.14, 138.29, 134.46, 131.31, 130.89, 130.18, 129.47, 128.47, 127.77, 126.46, 42.97, 38.98, 36.16.

Example 5

3,4-dihydro-3-methyl-4-oxo-N-(3(2H)-oxo-5-bromo-1,2-benzisoselenazol-2-yl)-ethyl-imidazo[5,1-d]-1,2,3,5-tetrazine-8-carboxamide (No. 5)

1) To a beaker was added 10.80 g of 2-amino-5-bromobenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 5,5'-dibromo-2,2'-diselanediyldibenzoic acid (8.37 g, 60%).

2) To 5,5'-dibromo-2,2'-diselanediyldibenzoic acid (5.58 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 5-bromo-2-selenochlorobenzoyl chloride (4.19 g, 63%).

3) Boc-ethylenediamine (1.60 g, 10 mmol) was dissolved in dichloromethane (10 mL), and 1.39 mL of triethylamine was added. A solution of 5-bromo-2-selenochlorobenzoyl chloride (3.33 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-5-bromo-1,2-benzisoselenazol-2-yl)-ethyl-1-carbamate (1.72 g, 41%).

4) To a 25 mL single-neck flask was added tert-butyl (3(2H)-oxo-5-bromo-1,2-benzisoselenazol-2-yl)-ethyl-1-carbamate (0.420 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-5-bromo-1,2-benzisoselenazol-3(2H)-one hydrochloride (0.338 g, 95%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 80%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-5-bromo-1,2-benzisoselenazol-3(2H)-one hydrochloride (267 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (151 mg, 61%). $^1$H NMR (400 MHz, DMSO-$d_6$) δ 8.84 (s, 1H), 8.66 (t, J=5.7 Hz, 1H), 8.12 (d, J=8.6 Hz, 1H), 7.92-7.84 (m, 1H), 7.74 (dd, J=8.5 Hz, 1H), 3.92 (t, J=5.8 Hz, 2H), 3.86 (s, 3H), 3.59 (q, J=5.8 Hz, 2H). $^{13}$C NMR (101 MHz, DMSO-$d_6$) δ 165.18, 159.93, 139.25, 139.13, 134.45, 130.21, 130.16, 129.25, 129.06, 128.57, 128.45, 118.74, 42.76, 39.05, 36.16.

Example 6

3,4-dihydro-3-methyl-4-oxo-N-(3(2H)-oxo-5-methyl-1,2-benzisoselenazol-2-yl)-ethyl-imidazo[5,1-d]-1,2,3,5-tetrazine-8-carboxamide (No. 6)

1) To a beaker was added 7.75 g of 2-amino-5-methylbenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 5,5'-dimethyl-2,2'-diselanediyldibenzoic acid (5.88 g, 54%).

2) To 5,5'-dimethyl-2,2'-diselanediyldibenzoic acid (4.28 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 5-methyl-2-selenochlorobenzoyl chloride (2.84 g, 53%).

3) Boc-ethylenediamine (1.60 g, 10 mmol) was dissolved in dichloromethane (10 mL), and 1.39 mL of triethylamine was added. A solution of 5-methyl-2-selenochlorobenzoyl chloride (2.68 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-5-methyl-1,2-benzisoselenazol-2-yl)-ethyl-1-carbamate (1.31 g, 37%).

4) To a 25 mL single-neck flask was added tert-butyl (3(2H)-oxo-5-methyl-1,2-benzisoselenazol-2-yl)-ethyl-1-carbamate (0.355 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-5-methyl-1,2-benzisoselenazol-3(2H)-one hydrochloride (0.262 g, 90%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 75%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-5-methyl-1,2-benzisoselenazol-3(2H)-one hydrochloride (231 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (147 mg, 68%). $^1$H NMR (400 MHz, DMSO-$d_6$) δ 8.84 (s, 1H), 8.66 (t, J=5.4 Hz, 1H), 7.88 (d, J=8.2 Hz, 1H), 7.64 (s, 1H), 7.42 (d, J=8.2 Hz, 1H), 3.92 (t, J=6.1 Hz, 2H), 3.86 (s, 3H), 3.59 (q, J=6.1 Hz, 2H), 2.39 (s, 3H). $^{13}$C NMR (101 MHz, DMSO-$d_6$) δ 166.56, 159.93, 139.14, 136.28, 135.22, 134.46, 132.69, 130.18, 128.46, 127.73, 127.32, 125.56, 42.80, 39.22, 36.16, 20.47.

Example 7

3,4-dihydro-3-methyl-4-oxo-N-(3(2H)-oxo-5-methoxy-1,2-benzisoselenazol-2-yl)-ethyl-imidazo[5,1-d]-1,2,3,5-tetrazine-8-carboxamide (No. 7)

1) To a beaker was added 8.35 g of 2-amino-5-methoxybenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition dropwise, the solution was reacted for another 2 h while being kept alkaline. After the reaction was completed, the mixture was acidified with hydrochloric acid and filtered to give a solid, and the solid was washed with water and then dried in a drying oven to give 5,5'-dimethoxy-2,2'-diselanediyldibenzoic acid (5.17 g, 45%).

2) To 5,5'-dimethoxy-2,2'-diselanediyldibenzoic acid (4.60 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 5-methoxy-2-selenochlorobenzoyl chloride (2.67 g, 47%).

3) Boc-ethylenediamine (1.60 g, 10 mmol) was dissolved in dichloromethane (10 mL), and 1.39 mL of triethylamine was added. A solution of 5-methoxy-2-selenochlorobenzoyl chloride (2.84 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-5-methoxy-1,2-benzisoselenazol-2-yl)-ethyl-1-carbamate (1.67 g, 45%).

4) To a 25 mL single-neck flask was added tert-butyl (3(2H)-oxo-5-methoxy-1,2-benzisoselenazol-2-yl)-ethyl-1-carbamate (0.371 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-5-methoxybenzo[d][1,2]selenoazo-3(2H)-one hydrochloride (0.271 g, 88%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 80%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-5-methoxy-1,2-benzisoselenazol-3(2H)-one hydrochloride (231 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (159 mg, 71%). $^1$H NMR (400 MHz, DMSO-$d_6$) δ 8.84 (s, 1H), 8.67 (t, J=5.7 Hz, 1H), 7.91 (d, J=8.8 Hz, 1H), 7.32 (d, J=2.7 Hz, 1H), 7.23 (dd, J=8.8, 2.7 Hz, 1H), 3.93 (t, J=6.0 Hz, 2H), 3.87 (s, 3H), 3.82 (s, 3H), 3.60 (q, J=6.0 Hz, 2H). $^{13}$C NMR (101 MHz, DMSO-$d_6$) δ 166.36, 159.93, 158.14, 139.14, 134.46, 130.43, 130.19, 128.72, 128.46, 126.80, 120.46, 109.69, 55.46, 42.96, 39.23, 36.16.

Example 8

3,4-dihydro-3-methyl-4-oxo-N-(3(2H)-oxo-6-methyl-1,2-benzisoselenazol-2-yl)-ethyl-imidazo[5,1-d]-1,2,3,5-tetrazine-8-carboxamide (No. 8)

1) To a beaker was added 7.75 g of 2-amino-6-methylbenzoic acid, followed by a mixed liquid of 15 mL of concentrated hydrochloric acid and 15 mL of water. The mixture was cooled in an ice bath to keep the reaction temperature at below 5° C. A solution of $NaNO_2$ (4.35 g dissolved in 10 mL of water) was slowly added dropwise. After completion of the addition dropwise, the mixture was reacted for another 2 h to give a diazonium salt solution for later use. 4 g of NaOH was added to 30 mL of water and dissolved by stirring at 50° C., and then 4.35 g of sodium hydrosulfite was added in small batches. After the mixture became clear, 4 g of selenium powder was added. After completion of the addition dropwise, the mixture was reacted for another 3 h to give a $Na_2Se_2$ solution for later use. The diazonium salt solution was added dropwise to the $Na_2Se_2$ solution under stirring, with the reaction temperature kept at below 5° C. After completion of the addition, the solution was reacted for another 2 h while being kept alkaline. After the reaction was completed, the mixture was acidified with hydrochloric acid and filtered to give a solid, and the solid was washed with water and then dried in a drying oven to give 4,4'-dimethyl-2,2'-diselanediyldibenzoic acid (5.88 g, 55%).

2) To 4,4'-dimethyl-2,2'-diselanediyldibenzoic acid (4.28 g, 10 mmol) were added thionyl chloride (20 mL) and 1 to 2 drops of DMF. The mixture was stirred at reflux for 5 h and concentrated under reduced pressure to evaporate thionyl chloride. The residue was recrystallized from petroleum ether (100 mL), and the mixture was filtered through celite. The filtrate was stored in a refrigerator to give a yellow needle-like crystal, i.e., 4-methyl-2-selenochlorobenzoyl chloride (2.84 g, 53%).

3) Boc-ethylenediamine (1.60 g, 10 mmol) was dissolved in dichloromethane (10 mL), and 1.39 mL of triethylamine was added. A solution of 4-methyl-2-selenochlorobenzoyl chloride (2.68 g, 10 mmol) in dichloromethane (10 mL) was slowly added dropwise to the mixture with cooling in an ice bath. The mixture was warmed to room temperature, reacted for 3 h, and concentrated under reduced pressure to evaporate the solvent. Diethyl ether was added, followed by stirring, and a white solid precipitated. The solid was washed successively with water and petroleum ether, dried, and purified by column chromatography (petroleum ether:dichloromethane:methanol=200:200:1) to give a yellow solid, i.e. tert-butyl (3(2H)-oxo-6-methyl-1,2-benzisoselenazol-2-yl)-ethyl-1-carbamate (1.85 g, 52%).

4) To a 25 mL single-neck flask was added tert-butyl (3(2H)-oxo-6-methyl-1,2-benzisoselenazol-2-yl)-ethyl-1-carbamate (0.355 g, 1.00 mmol), followed by a solution of 2 N hydrochloric acid in ethyl acetate (5 mL). The solution was reacted for 1 h, turning from clear to turbid, and a white precipitate formed. The mixture was subjected to suction filtration, and the filter cake was washed with ethyl acetate to give a white solid, i.e., 2-(2-aminoethyl)-6-methyl-1,2-benzisoselenazol-3(2H)-one hydrochloride (0.265 g, 91%).

5) TMZ (0.97 g, 5.0 mmol) was added in batches to concentrated sulfuric acid under stirring at room temperature. After completion of the addition, 8 mL of an aqueous solution of $NaNO_2$ (1.3 g, 18.8 mmol) was added dropwise with cooling in an ice bath to control the temperature at 0° C. After completion of the addition, the system solution was slowly stirred at room temperature, turning from a brownish-yellow liquid into a green gum and into a light yellow gum. The gum was poured into crushed ice and vigorously stirred until the solution turned into a white slurry. The slurry was subjected to suction filtration, and the filter cake was washed with ice water and dried to give a white amorphous solid, i.e. 3,4-dihydro-3-methyl-4-oxo-imidazo[5,1-d]-1,2,3,5-tetrazine-8-carboxylic acid (0.75 g, 80%).

6) 3,4-Dihydro-3-methyl-4-oxo-imidazo[5,1-d]-1,2,3,5-tetrazine-8-carboxylic acid (0.585 g, 3 mmol) was reacted with 30 mL of thionyl chloride and 2 drops of DMF for 5 h, and the solvent was evaporated under reduced pressure. A small amount of toluene was added, and toluene was evaporated under reduced pressure to give 3,4-dihydro-3-methyl-4-oxo-imidazo[5,1-d]-1,2,3,5-tetrazine-8-carbonyl chloride (0.545 g, 85%).

7) 2-(2-Aminoethyl)-6-methyl-1,2-benzisoselenazol-3(2H)-one hydrochloride (219 mg, 0.75 mmol) was reacted with triethylamine in dichloromethane for 1 h first, and a solution of 3,4-dihydro-3-methyl-4-oxo-imidazo[5,1-d]-1,2,3,5-tetrazine-8-carbonyl chloride (107 mg, 0.5 mmol) in dichloromethane was added with cooling in an ice bath. After completion of the addition, the mixture was warmed to room temperature, reacted overnight, and concentrated under reduced pressure to evaporate the solvent. The solid was washed with dichloromethane, water and acetone and dried to give the target compound as a white solid (153 mg, 71%). $^1H$ NMR (400 MHz, DMSO-$d_6$) δ 8.84 (s, 1H), 8.67 (t, J=5.7 Hz, 1H), 7.84 (s, 1H), 7.70 (d, J=7.9 Hz, 1H), 7.22 (d, J=7.5 Hz, 1H), 3.92 (t, J=6.0 Hz, 2H), 3.86 (s, 3H), 3.59 (q, J=5.9 Hz, 2H), 2.40 (s, 3H). $^{13}C$ NMR (101 MHz, DMSO) δ 166.55, 159.92, 141.55, 139.78, 139.13, 134.45, 130.18, 128.45, 127.05, 126.98, 125.68, 125.43, 42.70, 38.96, 36.15, 21.46.

Example 9: Study of In-Vitro Antitumor Activity of Compounds of the Present Disclosure The in-vitro growth inhibitory activity of compounds 1 to 8 of the present disclosure against human glioma cells (U87 and LN229), human hepatoma cells (SMMC-7721) and human pancreatic carcinoma cells (Panc1) was studied adopting the MTT method.

U87, LN229, SMMC-7721 and Panc1 cells growing at log phase were separately inoculated into a 96-well plate at a density of $5\times10^4$ cells/mL, 180 μL/well. After the cells were attached to the wall, 20 μL of a drug liquid was added to each well, so that the final concentrations of the drug were 0 μM, 5 μM, 10 μM, 20 μM and 50 μM. After 48 h of action, a 5 mg/mL MTT solution (20 μL/well) was added. After the cells were incubated in a $CO_2$ incubator for 3 to 4 h, the supernatant was carefully discarded. After the residual liquid was air-dried, acidified isopropanol (50 μL of concentrated hydrochloric acid dissolved in 500 mL of isopropanol) was added at 200 mL/well, and the plate was shaken on a shaker for 30 min. After the crystals were completely dissolved, absorbance OD values were measured by a microplate reader at 570 nm. The results are shown in Table 2.

$$\text{Cell viability }\% = (\text{drug-treated cell } OD - \text{blank group } OD) / (\text{control cell } OD - \text{blank group } OD) \times 100$$

$$\text{Cell killing rate }\% = 1 - \text{cell viability }\%$$

TABLE 2

Inhibitory activity ($IC_{50}$) of compounds 1 to 8 acting on U87 and LN229 cells for 48 h in vitro

| No. | $IC_{50}$ (μM) Cell lines U87 | LN229 | SMMC-7721 | Panc1 |
|---|---|---|---|---|
| TMZ | 373.06 ± 24.12 | >500 | — | — |
| 1 | 20.98 ± 3.07 | 14.41 ± 2.24 | 11.98 ± 1.57 | 17.81 ± 3.44 |
| 2 | >500 | 52.23 ± 10.72 | 16.41 ± 3.59 | 22.23 ± 8.78 |
| 3 | 20.43 ± 7.19 | 19.00 ± 1.30 | 25.43 ± 7.19 | 7.00 ± 8.30 |
| 4 | 133.60 ± 15.84 | 44.15 ± 6.09 | 5.60 ± 5.84 | 24.15 ± 11.9 |
| 5 | 35.78 ± 6.27 | 14.41 ± 3.89 | 7.77 ± 3.28 | 4.41 ± 2.89 |
| 6 | 19.25 ± 3.77 | 11.34 ± 0.82 | 11.25 ± 2.11 | 29.34 ± 0.42 |
| 7 | 47.00 ± 2.88 | 21.17 ± 1.28 | 27.00 ± 3.22 | 15.7 ± 6.22 |
| 8 | 20.36 ± 3.13 | 13.68 ± 2.52 | 3.35 ± 2.13 | 8.65 ± 3.52 |

The experimental results in Table 2 show that the $IC_{50}$ values of compound 1 and compounds 3 to 8 of the present disclosure were significantly lower than that of TMZ in the human glioma U87 cell line. In the human glioma LN229 cell line, the compounds of the present disclosure all showed good inhibitory activity; in particular, the $IC_{50}$ value of compound 6 was significantly lower than that of TMZ, and the $IC_{50}$ values of compounds 3, 5 and 8 were comparable to that of TMZ. In the human hepatoma SMMC-7721 cell line, the compounds of the present disclosure all showed good inhibitory activity; in particular, the $IC_{50}$ values of compounds 4, 5 and 8 were significantly lower than that of TMZ, and the $IC_{50}$ values of compounds 2 and 6 were comparable to that of TMZ. In the human pancreatic carcinoma Panc1 cell line, the compounds of the present disclosure all showed good inhibitory activity; in particular, the $IC_{50}$ values of compounds 3, 5 and 8 were significantly lower than that of TMZ, and the $IC_{50}$ values of the other compounds were comparable to that of TMZ.

Example 10: Study of In-Vivo Antitumor Activity of Compound 1 of the Present Disclosure This experiment examined the in-vivo antitumor activity of compound 1 (i.e. 3,4-dihydro-3-methyl-4-oxo-N-(3(2H)-oxo-benzisoselenazol-2-yl)-ethyl-imidazo[5,1-d]-1,2,3,5-tetra zine-8-carboxamide (No. 0409 in the animal experiment).

In this study, 4-week-old healthy female Balb/c nude mice weighing 12-17 g were randomly grouped, with 8 mice in each of a control group and a temozolomide group and 4 mice in each of a 0409 low-dose group and a 0409 high-dose group. A human glioma cell U87 suspension was prepared at $2\times10^7$/mL. Each nude mouse was inoculated with 0.1 mL of the suspension in the right armpit, that is, the quantity for inoculation was $2\times10^6$ cells/mouse. The tumor emergence rate was 100%. Dosing began on day 12 after inoculation and was performed for 11 consecutive days.

Figure 3:
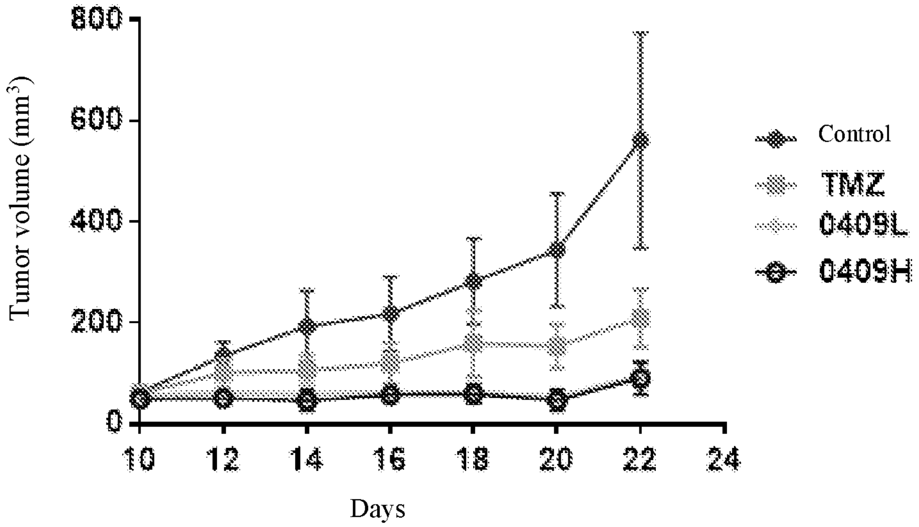
FIG. 3 shows the effect of compound 1 on the tumor volume in the tumor-bearing (U87) mice.
Figure 4:
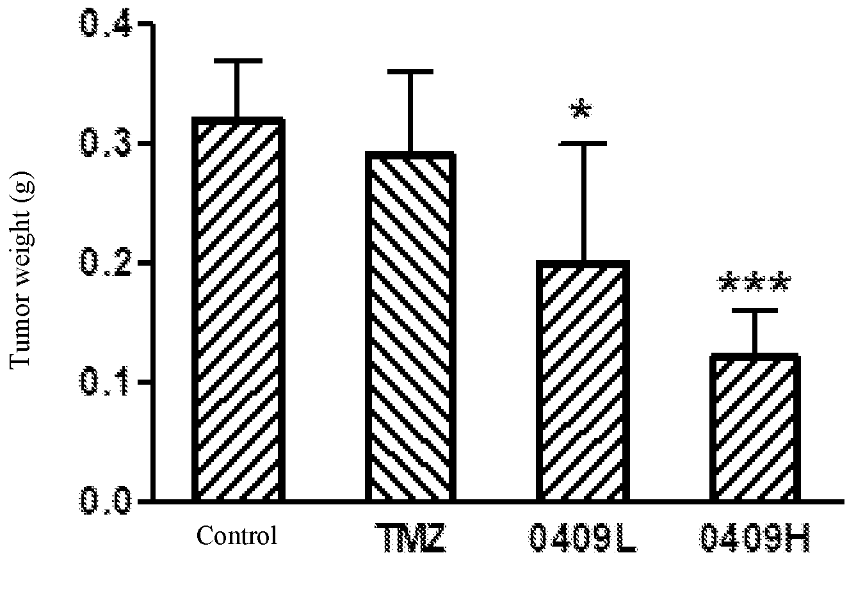
FIG. 4 shows the effect of compound 1 on the tumor weight in the tumor-bearing (U87) mice.

Dosages were as follows: the blank control group (5‰ sodium carboxymethylcellulose, administered orally once a day), the temozolomide group (30 $mg\cdot kg^{-1}$, i.g., q.d.), the 0409 low-dose group (45 $mg\cdot kg^{-1}$, i.g., q.d.), and the 0409 high-dose group (90 $mg\cdot kg^{-1}$, i.g., q.d.). The solvent for the temozolomide group, the 0409 low-dose group and the 0409 high-dose group was acetic acid-sodium acetate buffer solution (pH 4.5). That is, 18 g of sodium acetate was weighed out, and 9.8 mL of glacial acetic acid was added; the mixture was then added with water for dilution to 1000 mL. The solvent was freshly prepared when needed each day. The status of the mice was observed daily for 22 consecutive days, and body weights and tumor volumes were recorded. Tumor volumes of 100 $mm^3$ were used as a criterion to determine whether tumors had emerged in the mice or not. The results are shown in Table 3 and FIGS. 2, 3 and 4.

TABLE 3

Tumor volumes and weights of nude mice in each group at the end of the experiment and tumor inhibition rates

| Group | Tumor volume ($mm^3$) | Tumor weight (g) | Tumor proliferation inhibition rate (%) |
|---|---|---|---|
| Blank control group | 561.49 ± 213.64 | 0.32 ± 0.05 | — |
| Temozolomide group | 209.18 ± 57.83*** | 0.29 ± 0.07 | 62.75 |
| 0409 low-dosage group | 96.70 ± 24.08*** | 0.20 ± 0.10* | 82.78 |
| 0409 high-dose group | 90.00 ± 32.64*** | 0.12 ± 0.04*** | 83.97 |

The data are expressed as mean values ± standard deviations.

*P < 0.05, P < 0.01 and *P < 0.001 indicate statistical differences from the control group.

Conclusion

Figure 2:
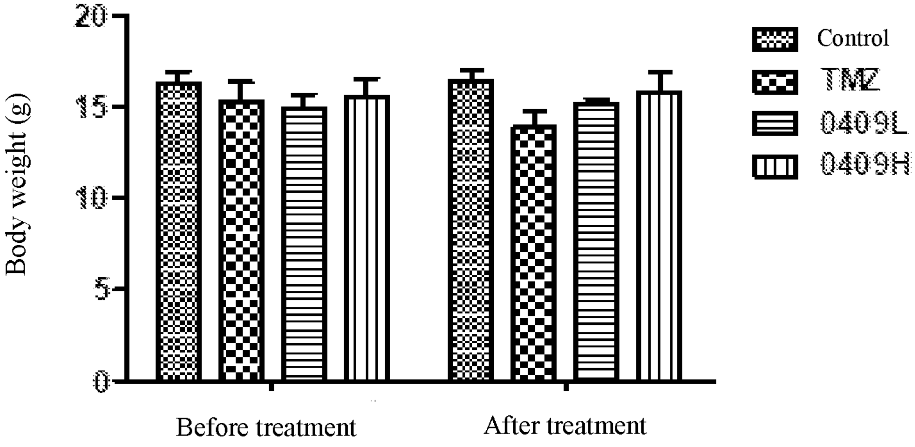
FIG. 2 shows the effect of compound 1 on the body weight of tumor-bearing (U87) mice.

FIG. 2 shows changes in the body weight of the mice in each group on day 11 after administration relative to that before administration during administration. The body weights of the mice in the control group, the temozolomide (TMZ) group, the 0409 low-dose (0409L) group and the 0409 high-dose (0409H) group on day 11 after administration were 1.01 times, 0.91 times, 1.02 times and 1.02 times those of the mice before administration, respectively. The body weight of the TMZ group was significantly reduced, reflecting the toxic reaction resulted from TMZ, and the drugs in the other groups had no significant toxic and side effects on the mice.

The tumor volumes and tumor weights of the nude mice were analyzed statistically. The results are shown in Table 3, FIG. 3 and FIG. 4. The tumor volumes and tumor weights in each administration group were statistically different from those of the control group. Firstly, the TMZ group had a tumor volume of 209.18±57.83 $mm^3$ and a tumor weight of 0.29±0.07 g; the 0409 low-dose group had a tumor volume of 96.70±24.08 $mm^3$ and a tumor weight of 0.20±0.10 g; the 0409 high-dose group had a tumor volume of 90.00±32.64 $mm^3$ and a tumor weight of 0.12±0.04 g. Compared with temozolomide, 0409 has significantly improved efficacy. Secondly, the tumor volumes and tumor weights of the 0409 low-dose group and the 0409 high-dose group were reduced sequentially, and the tumor inhibition rates of the 0409 low-dose group and the 0409 high-dose group were 82.78% and 83.97% respectively, indicating that the tumor growth inhibition effect of 0409 was concentration-dependent to a certain degree.

In addition, low-dosage 0409 (20 $mg\cdot kg^{-1}$, i.v.) and TMZ (10 $mg\cdot kg^{-1}$, i.v.) were synchronously used for an assay to determine the volume tumor inhibition rate. The results are shown in Table 4.

TABLE 4

Tumor volume inhibition rate results of low-dosage 0409 (20 mg · $kg^{-1}$, i.v.) and TMZ (10 mg · $kg^{-1}$, i.v.)

| Tumor volume inhibition rate (%) | Day 10 | Day 11 | Day 12 | Day 13 | Day 14 | Day 15 | Day 16 | Day 17 | Day 18 |
|---|---|---|---|---|---|---|---|---|---|
| TMZ | 36.69 | 58.86 | 38.02 | 38.14 | 24.37 | 63.87 | 54.29 | 51.04 | 54.55 |
| 1 | 74.77 | 73.84 | 69.78 | 79.84 | 81.42 | 80.49 | 78.49 | 82.30 | 81.72 |
| 2 | 84.98 | 84.64 | 82.90 | 85.82 | 86.34 | 85.81 | 84.38 | 86.66 | 86.45 |
| 3 | 57.85 | 67.11 | 68.40 | 58.78 | 72.29 | 72.69 | 78.57 | 74.77 | 73.84 |
| 4 | 73.47 | 75.25 | 74.48 | 68.82 | 73.96 | 80.57 | 84.32 | 84.72 | 81.05 |
| 5 | 27.13 | 26.96 | 36.82 | 36.77 | 44.62 | 59.52 | 61.18 | 58.45 | 64.42 |
| 6 | 91.47 | 91.63 | 90.11 | 88.52 | 88.01 | 88.94 | 87.54 | 88.46 | 88.28 |
| 7 | 21.96 | 29.68 | 37.52 | 48.01 | 45.55 | 51.38 | 59.70 | 46.34 | 54.68 |
| 8 | 86.55 | 86.16 | 87.20 | 88.20 | 92.48 | 87.74 | 87.01 | 88.52 | 89.11 |

Example 11: Pharmacodynamic Study of Compounds 1, 3, 6 and 8 in Human Glioma Cell U87 Subcutaneous Models Established with Balb/C Nude Mice With the same experimental model and operation process as Example 10, the inhibitory effects of compound 1, compound 3, compound 6, compound 8 and the TMZ administered alone on tumor growth in the human glioma cell U87 subcutaneous model of Balb/c Nude were explored simultaneously. The route of administration was intragastric administration (i.p., q.d.×14 days). The results were as follows:

1) Compound 1 (20 mg/Kg), compound 3 (20 mg/Kg), compound 6 (20 mg/Kg), and compound 8 (20 mg/Kg) did not cause weight loss at the dosages of this study. This indicated that this type of drugs did not have significant toxic and side effects on the nude mice.

From day 4 after administration, the tumor inhibition rate of the compound 6 group was significantly higher than those of the other administration groups, and on day 7 after administration, the tumor inhibition rates of compound 3, compound 6 and compound 8 groups were all 80% or higher. At the end of the experiment, the tumor volume inhibition rates of the administration groups, i.e. the TMZ group, the compound 1 group, the compound 3 group, the compound 6 group and the compound 8 group, were 14.26%, 81.42%, 88.01%, 92.48% and 82.68%, respectively. The results are shown in Table 5:

TABLE 5

Tumor inhibition rate (%) of each group

| Days | Day 1 | Day 4 | Day 7 | Day 10 | Day 14 |
|---|---|---|---|---|---|
| TMZ | 6.77 | 38.14 | 54.29 | 46.23 | 14.26 |
| Compound 1 | 5.86 | 58.78 | 78.57 | 74.77 | 81.42 |
| Compound 3 | −9.91 | 47.90 | 87.76 | 91.47 | 88.01 |
| Compound 6 | 9.05 | 68.76 | 84.09 | 86.55 | 92.48 |
| Compound 8 | −0.20 | 58.48 | 83.03 | 80.92 | 82.68 |

Since thioredoxin reductase is widely and highly expressed in tumor tissues and can be selectively recognized by the aryl-fused isoselenazole compound of the present disclosure, the aryl-fused isoselenazole compound of the present disclosure showed a good targeting property. The drugs of the present disclosure can well inhibit the growth of glioma cells both in vitro and in vivo, significantly expanding the range of application of existing aryl-fused isoselenazole compounds.

Example 12: Study of In-Vitro Antitumor Activity of Compounds of the Present Disclosure Referring to the method of example 9, two tumor cell lines, U251MG and U251TR human glioma cells, were selected, and temozolomide and the compounds of the present disclosure were subjected to in-vitro anti-cancer activity screening using the SRB method. The $IC_{50}$ value (μM) of each compound is shown in Table 6 below:

TABLE 6

In-vitro anti-tumor $IC_{50}$ results (μM) of compounds

| Compounds | U251MG | U251TR |
|---|---|---|
| TMZ* | 430.99 ± 25.79 | >500 |
| BS** | ND | ND |
| 1 | 48.94 ± 9.33 | 51.90 ± 21.87 |
| 2 | 363.23 ± 21.40 | >500 |
| 3 | 15.40 ± 1.25 | 35.54 ± 4.97 |
| 4 | 125.53 ± 13.26 | >500 |
| 5 | 61.67 ± 5.79 | 56.25 ± 11.66 |
| 6 | 1.26 ± 0.83 | 29.36 ± 3.21 |
| 7 | 153.69 ± 5.64 | >500 |
| 8 | 9.13 ± 1.52 | 16.24 ± 1.67 |

Note:
*positive drug for gliomas, i.e., temozolomide;
**TrxR inhibitor positive drug, i.e Butaselen;
ND: not determined The experimental results in Table 6 show that compounds 1, 3, 6 and 8 of the present disclosure were all below 5 μM in terms of TrxR inhibition, and the TrxR inhibitory activity of compound 1 among them approximated that of the TrxR inhibitor positive drug BS. In human glioma cell lines U251MG and U251TR, the $IC_{50}$ values of the compounds of the present disclosure were better than that of TMZ, which indicates that the aryl-fused isoselenazole compounds containing a tetrazine substituent showed good activity against glioma cell lines. Compounds 1, 3, 5, 6 and 8 of the present disclosure had very low $IC_{50}$ values in both cell lines, particularly the drug-resistant strain U251TR, showing very strong inhibitory activity.

Example 13: Determination of Thioredoxin Reductase (TrxR) Activity of Compounds of the Present Disclosure The determination method was as follows:

1. The cellular total protein (i.e. thioredoxin reductase) was extracted and the concentration was determined. 30 μg of protein sample was added to a 96-well plate (3 replicate wells per concentration), and the volume was made up to 80 μL with 0.1 M sodium phosphate buffer. The protein samples were incubated in an oven at 37° C. for 30 min.

2. 20 μL of 5 mM NADPH was added (an equivalent volume of 0.1 M sodium phosphate buffer solution was added to the control group), and finally, 100 μL of 10 mM DTNB and test compounds ($IC_{50}$ was routinely determined using 5 or more concentrations) were added. The absorbance was immediately measured at 405 nm using a microplate reader (FlexStation 3, Molecular Devices). Shaking was performed for 10 s before the first reading, and determination was performed once every 15 s, 30 times in total. The maximum reaction rate was taken as an enzymatic activity index. The experiment was independently repeated three times.

The determination results are shown in Table 7 below:

TABLE 7

| Inhibitory activity against thioredoxin reductase ($IC_{50}$ (μM)) | |
|---|---|
| Compounds | TrxR |
| TMZ* | >30 |
| BS** | 1.14 ± 0.17 |
| 1 | 2.01 ± 0.16 |
| 2 | 21.25 ± 5.81 |
| 3 | 4.59 ± 0.57 |
| 4 | 18.74 ± 3.29 |
| 5 | 7.35 ± 0.66 |
| 6 | 5.76 ± 0.38 |
| 7 | 15.02 ± 2.74 |
| 8 | 3.88 ± 0.79 |

Note:
*temozolomide;
**TrxR inhibitor positive drug, i.e. Butaselen

The determination results shows that the compounds of the present disclosure had good inhibitory activity against thioredoxin reductase (TrxR); in particular, the $IC_{50}$ values of compounds 1, 3, 5, 6, and 8 were in the same order of magnitude as that of the TrxR inhibitor positive drug Butaselen, showing excellent TrxR inhibitory activity. It is expected that the aryl-fused isoselenazole compounds of the present disclosure can be used as a TrxR inhibitor for the treatment or alleviation of a disease or condition associated with upregulated expression or increased activity of TrxR.

Examples of the present disclosure have been described above. However, the present disclosure is not limited thereto. Any modification, equivalent, improvement and the like made without departing from the spirit and principle of the present disclosure shall fall within the protection scope of the present disclosure.

The invention claimed is:

1. An aryl-fused isoselenazole compound containing a tetrazine substituent represented by formula (I) or a pharmaceutically acceptable salt thereof:

(I)

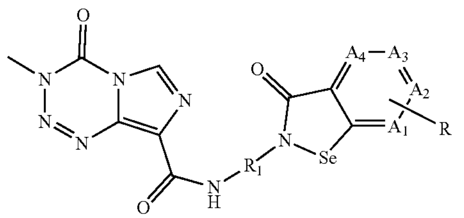

wherein $A_1$, $A_2$, $A_3$ and $A_4$ are identical or different and are each independently selected from CR and N, with the proviso that no more than one of $A_1$, $A_2$, $A_3$ and $A_4$ is N;

wherein R is selected from hydrogen, cyano, hydroxy, halogen, and nitro, or R is selected from amino, sulfhydryl, amido, alkyl, cycloalkyl, alkoxy, heterocyclyl, aryl and heteroaryl, which are substituted with one or more Ra, each Ra is independently selected from hydrogen, cyano, hydroxy, halogen, amino, nitro, sulfhydryl, alkyl, cycloalkyl, alkoxy, aryl, and heteroaryl; and $R_1$ is alkylene.

2. The compound or the pharmaceutically acceptable salt thereof according to claim 1, wherein the compound has a structure represented by formula (II):

(II)

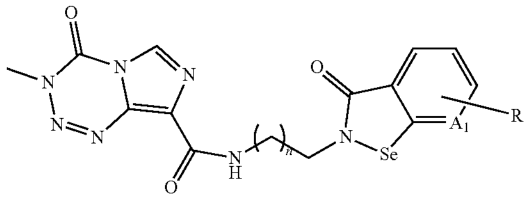

wherein $A_1$ is selected from CH and N; and n is 1, 2, 3, 4, 5, or 6.

3. The compound or the pharmaceutically acceptable salt thereof according to claim 1, wherein the pharmaceutically acceptable salt is an acid addition salt formed from the compound and an inorganic or organic acid, the inorganic acid being selected from at least one of hydrochloric acid, hydrofluoric acid, hydrobromic acid, hydroiodic acid, perchloric acid, sulfuric acid, pyrosulfuric acid, phosphoric acid, and nitric acid, and the organic acid being selected from at least one of formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptonic acid, glycerophosphoric acid, aspartic acid, sulfosalicylic acid, hemisulfuric acid, and thiocyanic acid;

or, the pharmaceutically acceptable salt is an alkali metal salt, alkaline earth metal salt or ammonium salt of the compound, or a salt formed from the compound and an organic base providing physiologically acceptable cations.

4. The compound or the pharmaceutically acceptable salt thereof according to claim 1, wherein:

R is selected from hydrogen, cyano, hydroxy, halogen, and nitro, or from amino, sulfhydryl, amido, $C_{1-10}$ alkyl, $C_{3-10}$ cycloalkyl, $C_{1-10}$ alkoxy, 3-10 membered heterocyclyl, $C_{6-14}$ aryl and 5-14 membered heteroaryl, which are substituted with one or more Ra, each Ra is independently from each other selected from hydrogen, cyano, hydroxy, halogen, amino, nitro, sulfhydryl, $C_{1-10}$ alkyl, $C_{3-10}$ cycloalkyl, $C_{1-10}$ alkoxy, 3-10 membered heterocyclyl, $C_{6-14}$ aryl, and 5-14 membered heteroaryl; $R_1$ is selected from $C_{1-10}$ alkylene.

5. The compound or the pharmaceutically acceptable salt thereof according to claim 4, wherein:

R is selected from hydrogen, halogen, or from $C_{1-6}$ alkyl, $C_{3-6}$ cycloalkyl, $C_{1-6}$ alkoxy, phenyl and pyridyl, which are substituted with one or more Ra, each Ra is independently from each other selected from hydrogen, halogen, $C_{1-6}$ alkyl, $C_{3-6}$ cycloalkyl, $C_{1-6}$ alkoxy, phenyl, and pyridyl; and $R_1$ is selected from $C_{1-6}$ alkylene.

6. The compound or the pharmaceutically acceptable salt thereof according to claim 5, wherein:

R is selected from hydrogen, halogen, $C_{1-6}$ alkyl, and $C_{1-6}$ alkoxy.

7. The compound or the pharmaceutically acceptable salt thereof according to claim 6, wherein:

R is selected from hydrogen, fluorine, chlorine, bromine, iodine, methyl, ethyl, n-propyl, isopropyl, n-butyl, isobutyl, tert-butyl, n-pentyl, isopentyl, methoxy, ethoxy, n-propoxy, isopropoxy, n-butoxy, isobutoxy, tert-butoxy, n-pentoxy, and isopentoxy.

8. The compound or the pharmaceutically acceptable salt thereof according to claim 2, wherein:

R is selected from hydrogen, halogen, $C_{1-6}$ alkyl, and $C_{1-6}$alkoxy.

9. The compound or the pharmaceutically acceptable salt thereof according to claim 8, wherein:

R is selected from hydrogen, fluorine, chlorine, bromine, iodine, methyl, ethyl, n-propyl, isopropyl, n-butyl, isobutyl, tert-butyl, n-pentyl, isopentyl, methoxy, ethoxy, n-propoxy, isopropoxy, n-butoxy, isobutoxy, tert-butoxy, n-pentoxy, and isopentoxy.

10. The compound or the pharmaceutically acceptable salt thereof according to claim 9, selected from compounds 1 to 8 listed in the following table:

| No. | Structure |
|---|---|
| 1 | 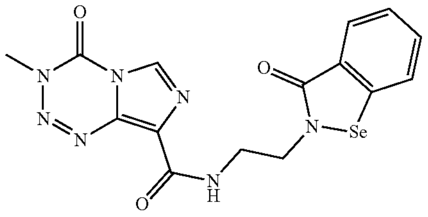 [SMILES: Cn1nnc2c(C(=O)NCCn3[se]c4ccccc4c3=O)ncn2c1=O] |
| 2 | 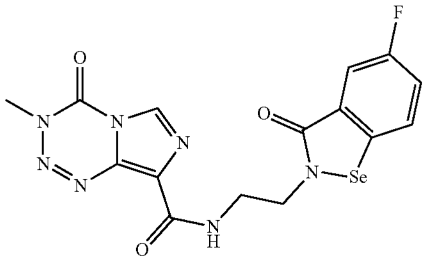 [SMILES: Cn1nnc2c(C(=O)NCCn3[se]c4ccc(F)cc4c3=O)ncn2c1=O] |
| 3 | 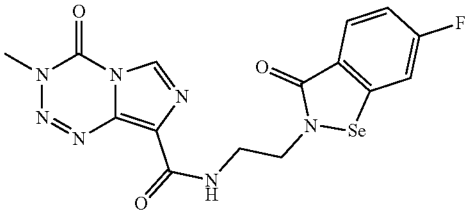 [SMILES: Cn1nnc2c(C(=O)NCCn3[se]c4cc(F)ccc4c3=O)ncn2c1=O] |

-continued

| No. | Structure |
|---|---|
| 4 | 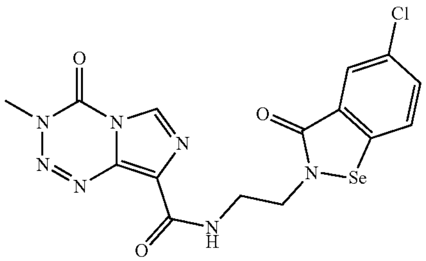 [SMILES: Cn1nnc2c(C(=O)NCCn3[se]c4ccc(Cl)cc4c3=O)ncn2c1=O] |
| 5 | 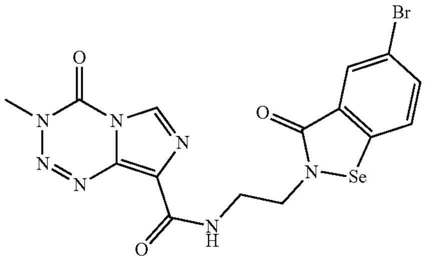 [SMILES: Cn1nnc2c(C(=O)NCCn3[se]c4ccc(Br)cc4c3=O)ncn2c1=O] |
| 6 | 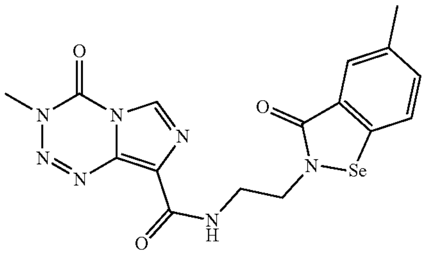 [SMILES: Cc1ccc2[se]n(CCNC(=O)c3ncn4c(=O)n(C)nnc34)c(=O)c2c1] |
| 7 | 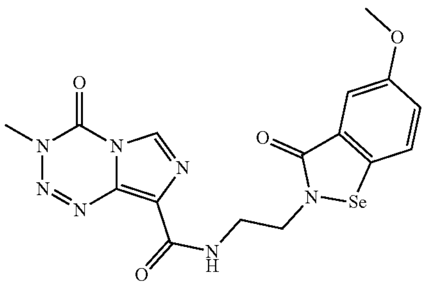 [SMILES: COc1ccc2[se]n(CCNC(=O)c3ncn4c(=O)n(C)nnc34)c(=O)c2c1] |
| 8 | 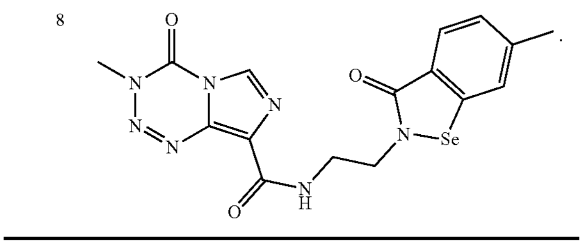 |

11. The compound or the pharmaceutically acceptable salt thereof according to claim 3, wherein the pharmaceutically acceptable salt is a salt formed from the compound and at least one selected from sodium ion, potassium ion, calcium ion, magnesium ion, morpholine, piperidine, triethylamine, tripropylamine, tributylamine, diisopropylamine, diisopropylethylenediamine, pyridine, dimethylamine, diethylamine, N-methylglucamine, dimethylglucamine, ethylglucamine, lysine, dicyclohexylamine, 1,6-hexanediamine, ethanolamine, glucosamine, meglumine, sarcosine, serinol, trihydroxymethylaminomethane, aminopropanediol, and 1-amino-2,3,4-butanetriol.

12. A preparation method for the compound according to claim 1, comprising the following steps:

1) diazotizing an amino group in a compound A, followed by reacting with $Na_2Se_2$ to prepare a compound B:

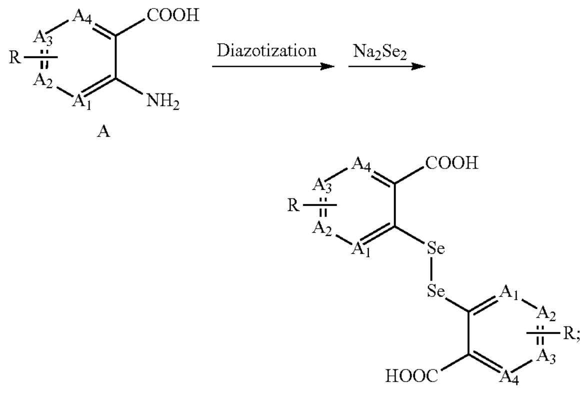

A

B wherein $A_1$, $A_2$, $A_3$, $A_4$, R and $R_1$ have the definitions described in claim 1;

2) reacting the compound B with thionyl chloride to prepare a compound C:

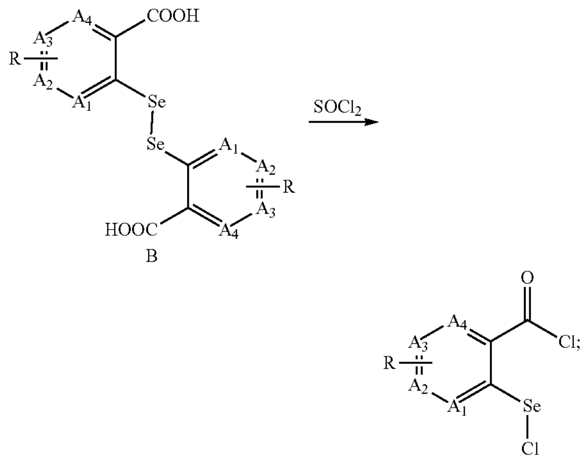

B

C 3) reacting the compound C with $H_2N—R_1—NHBoc$ to prepare a compound D:

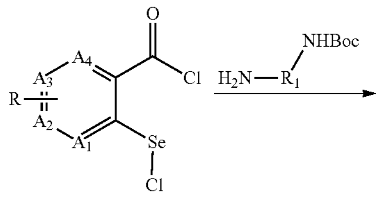

C

-continued

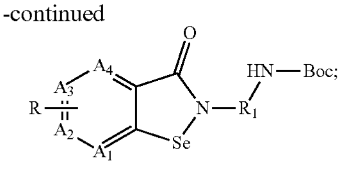

D wherein Boc represents tert-butyloxycarbonyl;

4) deprotection of the Boc protective group of the compound D in the presence of an acid to prepare a compound E:

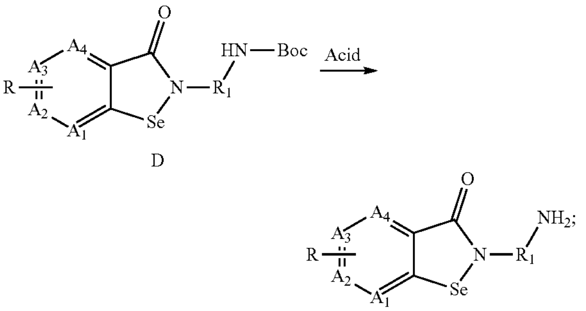

D

E and 5) reacting the compound E with a compound F to prepare the compound represented by formula (I):

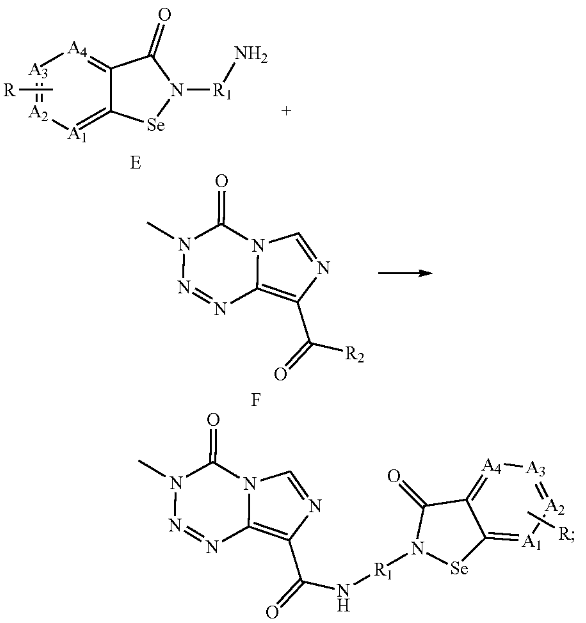

E

F (I)

wherein in the compound F, $R_2$ is selected from chlorine, bromine, hydroxy, and $—OR_3$, wherein $R_3$ is selected from $C_{1-6}$ alkyl, succinimidyl, tert-butyloxycarbonyl, methylsulfonyl, p-nitrobenzenesulfonyl, p-toluenesulfonyl, and isobutyloxycarbonyl.

13. The preparation method according to claim 12, characterized in that, the compound F is commercially available or can be obtained by using a conventional method in the art, or is prepared through the following steps:

a) allowing compound TMZ (i.e. temozolomide) to react under the action of sulfuric acid and sodium nitrite to give a compound F-1:

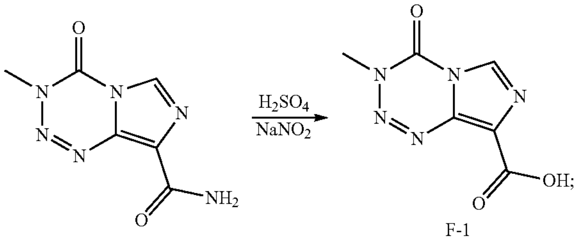

TMZ

F-1 and optional step b): reacting the compound F-1 with thionyl chloride or dibromosulfoxide in the presence of a catalytic amount of DMF to give a compound F-2:

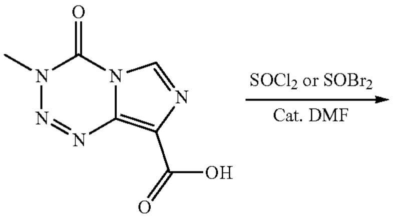

F-1

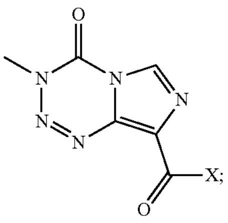

F-2
wherein X is Cl or Br or optional step c): allowing the compound F-1 to further react to give the compound F in which $R_2$ is —$OR_3$, wherein $R_3$ is $C_{1-6}$ alkyl, succinimidyl, tert-butoxycarbonyl, methanesulfonyl, p-nitrobenzenesulfonyl, p-toluenesulfonyl, or isobutyloxycarbonyl;

step c) is selected from step c-1), step c-2), step c-3), step c-4) and step c-5) below;

step c-1): reacting the compound F-1 with $R_4OH$ under the action of an acid to give a compound F-3:

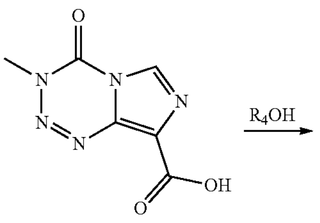

F-1

-continued

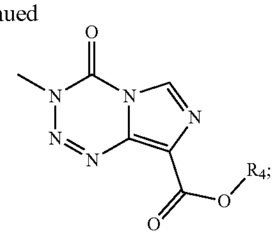

F-3 wherein $R_4$ is $C_{1-6}$alkyl;

step c-2): reacting the compound F-1 with $R_5Cl$ under the action of a base to give a compound F-4:

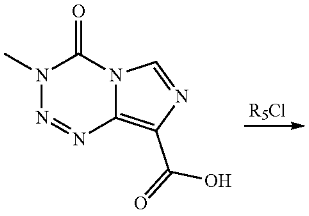

F-1

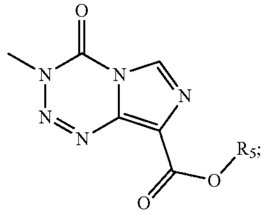

F-4 wherein $R_5$ is methylsulfonyl, p-nitrobenzenesulfonyl or p-toluenesulfonyl;

step c-3): reacting the compound F-1 with N-hydroxysuccinimide to give a compound F-5:

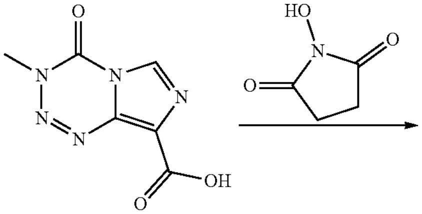

F-1

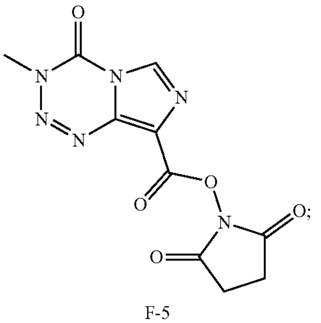

F-5 step c-4): reacting the compound F-1 with di-tert-butyl dicarbonate to give a compound F-6

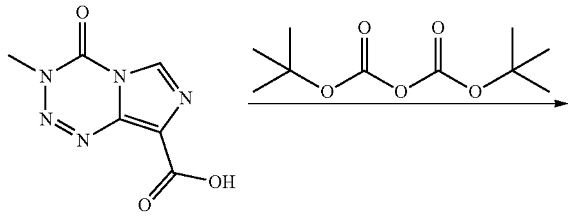

F-1

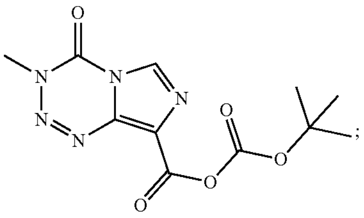

F-6 and step c-5): reacting the compound F-1 with isobutyl chloroformate to give a compound F-7:

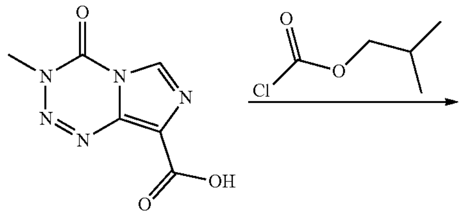

F-1

-continued

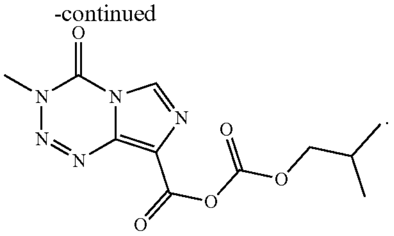

F-7

14. A pharmaceutical composition, wherein the pharmaceutical composition comprises the compound or the pharmaceutically acceptable salt thereof according to claim 1 and a pharmaceutically acceptable carrier.

15. The pharmaceutical composition according to claim 14, wherein the compound or the pharmaceutically acceptable salt thereof according to claim 1 and a pharmaceutically acceptable sustained/controlled-release carrier can be prepared into a sustained/controlled-release preparation according to a conventional preparation method for sustained/controlled-release preparations.

16. The pharmaceutical composition according to claim 14, wherein the pharmaceutical composition is suitable for enteral, topical or parenteral administration.

17. The pharmaceutical composition according to claim 16, wherein the pharmaceutical composition is administrated by oral administration, injection, implantation, topical application, spray, or inhalation.

18. The pharmaceutical composition according to claim 17, wherein the pharmaceutical composition is administrated by oral administration, the oral pharmaceutical composition in the form of a tablet, a capsule, a pill, an oral liquid preparation, granules, an injection, a topical preparation, or a powder.

19. A method for treating a tumor, comprising administrating the compound or the pharmaceutically acceptable salt thereof according to claim 1 to a subject in need thereof, wherein the tumor is selected from brain glioma, liver cancer, and pancreatic cancer.

* * * * *